United States Patent [19]

Collington et al.

[11] Patent Number: 5,039,673
[45] Date of Patent: Aug. 13, 1991

[54] AMINOCYCLOPENTYL ETHERS AND THEIR PREPARATION AND PHARMACEUTICAL FORMULATION

[75] Inventors: Eric W. Collington, Knebworth; Harry Finch, Letchworth; Roger Hayes, Potters Bar; Keith Mills, Ware; David F. Woodings, Felixstowe, all of England

[73] Assignee: Glaxo Group Limited, London, England

[21] Appl. No.: 397,118

[22] Filed: Aug. 22, 1989

Related U.S. Application Data

[63] Continuation-in-part of Ser. No. 210,419, Jun. 21, 1988, abandoned.

[30] Foreign Application Priority Data

Jun. 22, 1987 [GB] United Kingdom ............... 8714570
Jun. 22, 1987 [GB] United Kingdom ............... 8714571
Nov. 29, 1988 [GB] United Kingdom ............. 8827795.9

[51] Int. Cl.[5] .................. C07D 223/04; A61K 31/55
[52] U.S. Cl. .................................. 514/211; 514/212; 514/227.5; 514/237.8; 514/238.2; 514/234.2; 514/255; 514/315; 514/331; 514/428; 540/544; 540/610; 544/58.1; 544/58.2; 544/159; 544/168; 544/396; 544/399; 544/400; 546/232; 546/234; 546/239; 548/568; 548/569; 548/573
[58] Field of Search ............... 548/568, 569, 573; 540/232, 234, 239, 610, 544; 544/159, 168, 396, 399, 400, 58.1, 58.2; 514/211, 212, 428, 315, 331, 227.5, 255, 237.8, 238.2, 239.2

[56] References Cited

U.S. PATENT DOCUMENTS 4,409,213 10/1983 Collington et al. .................. 514/211
4,447,428 5/1984 Collington et al. .................. 514/211
4,613,597 9/1986 Collington et al. .................. 514/211

FOREIGN PATENT DOCUMENTS 296802 12/1988 European Pat. Off. ............ 514/211
2159816 12/1985 United Kingdom ................ 514/211

OTHER PUBLICATIONS

Matthews et al., *J. Org. Chem.*, 48, 4, 1983.

Primary Examiner—Robert Gerstl
Attorney, Agent, or Firm—Bacon & Thomas

[57] ABSTRACT

Compounds are described of the formula (1)

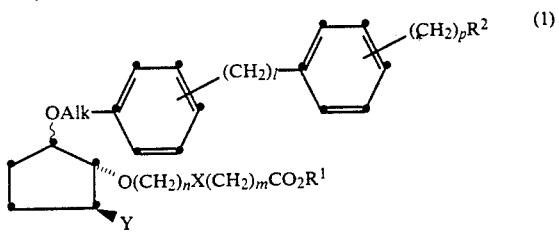

where:
$R^1$ is a hydrogen atom or a methyl group;
X is cis or trans —CH=CH— or —$CH_2CH_2$—, m is 2, 3 or 4 and n is 1; or X is trans —CH=CH—, m is zero and n is 3;
Y is a saturated heterocyclic amino group;
Alk is a $C_{1-5}$alkyl chain;
l is zero or 1;
p is zero, 1, 2, 3 or 4;
$R^2$ is a hydroxyl group or a group selected from —O-$COR^3$, —$CO_2R^3$, $CONR^3R^4$, —$SO_2NR^3R^4$, —$NHCOR^3$, —$NHSO_2R^5$, —$SO_2R^5$, —$SR^5$, —$NR^3R^4$, —$COR^5$, —$NHCONR^3R^4$ and —$NHCSNH_2$; and their physiologically acceptable salts, solvates and cyclodextrin complexes.

These compounds inhibit blood platelet aggregation, bronchoconstriction and vasoconstriction and may be formulated for use as antithrombotic agents.

11 Claims, No Drawings

AMINOCYCLOPENTYL ETHERS AND THEIR PREPARATION AND PHARMACEUTICAL FORMULATION

This application is a continuation-in-part of application Ser. No. 07/210,419, filed on June 21, 1988 now abandoned.

The endoperoxide prostaglandins $G_2$ and $H_2$ and thromboxane $A_2$ are naturally occurring reactive metabolites of arachidonic acid in human platelets. They are not only potent aggregatory agents but are also constrictors of vascular and bronchial smooth muscle, and therefore substances which antagonize their effects are of considerable interest in human medicine.

In GB-A-2159816 we have described a novel class of aminocyclopentane derivatives represented hereinafter by formula (A)

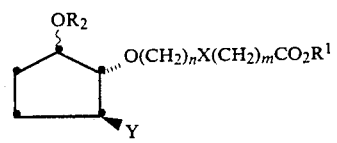

having endoperoxide and thromboxane-antagonist activity. The moiety $R^2$ therein covers a variety of groupings including straight or branched $C_{1-5}$alkyl substituted by phenyl which may itself be substituted by inter alia phenyl (optionally substituted by $C_{1-4}$alkyl, $C_{1-4}$alkoxy or phenyl) or phenyl$C_{1-3}$alkyl. Although the compounds of GB-A-2159816 exhibit good endoperoxide and thromboxane antagonist activity, duration studies have shown compounds exemplified therein to be only short-acting.

We have now surprisingly found that substitution of the second phenyl group within $R^2$ above by selected groupings provides novel compounds which have an advantageous profile of action with respect to compounds of GB-A-2159816. More particularly, the new compounds of the present invention have improved endoperoxide and thromboxane antagonist activity and/or duration of action.

The present invention thus provides compounds of the general formula (1)

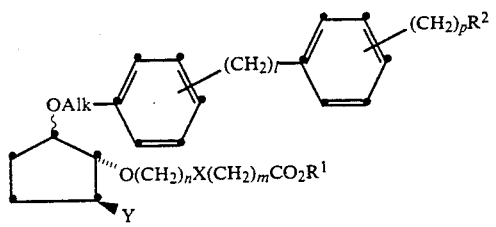

wherein:
$R^1$ is a hydrogen atom or a methyl group;
X is cis or trans —CH=CH— or —CH$_2$CH$_2$—, m is 2, 3 or 4 and n is 1; or X is trans —CH=CH—, m is zero and n is 3;
Y is a saturated heterocyclic amino group (attached to the cyclopentane ring via the nitrogen atom) which has 5-8 ring members and (a) optionally contains in the ring —O—, —S—, —SO$_2$—, or —NR$^{3a}$—; and/or (b) is optionally substituted by one or more $C_{1-4}$ alkyl groups;

Alk is a straight or branched $C_{1-5}$ alkyl chain;
l is zero or 1;
p is zero, 1, 2, 3 or 4;
$R^2$ is a hydroxyl group or a group selected from —OCOR$^3$, —CO$_2$R$^3$, —CONR$^3$R$^4$, —SO$_2$NR$^3$R$^4$, —NHCOR$^3$, —NHSO$_2$R$^5$, —SO$_2$R$^5$, —SR$^5$, —SR$^5$, —NR$^3$R$^4$, —COR$^5$, —NHCONR$^3$R$^4$ and —NHCSNH$_2$;
$R^3$, $R^{3a}$ and $R^4$, which may be the same or different, represent a hydrogen atom or a $C_{1-4}$ alkyl or $C_{7-10}$ aralkyl group; and
$R^5$ is a $C_{1-4}$ alkyl group; and the physiologically acceptable salts, solvates and cyclodextrin complexes thereof.

The structural formulae herein are to be understood to include the enantiomers of each of the compounds concerned as well as mixtures of the enantiomers including racemates, even through the precise structures as set out only relate to one enantiomer.

It will be appreciated that the present invention includes compounds of formula (1A) and (1B):

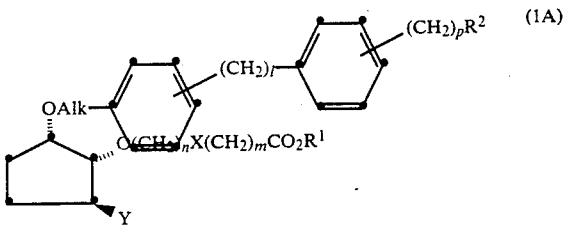

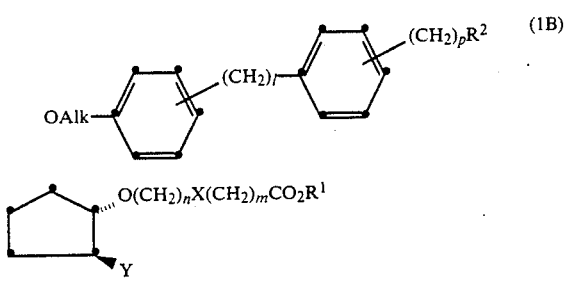

Suitable physiologically acceptable salts of the compounds of general formula (1) include acid addition salts derived from inorganic and organic acids, such as hydrochlorides, hydrobromides, sulfates, phosphates, maleates, tartrates, citrates, benzoates, 2-chlorobenzoates, p-toluenesulphonates, methanesulphonates, salicylates, fumarates, lactates, hydroxynaphthalenecarboxylates (e.g. 1-hydroxy or 3-hydroxy-2-naphthalenecarboxylates) or furoates. When $R^1$ is a hydrogen atom, the compounds may also form salts with suitable bases. Examples of such salts are alkali metal (e.g. sodium and potassium), alkaline earth metal (e.g. calcium or magnesium), ammonium and substituted ammonium (e.g. dimethylammonium, triethylammonium, 2-hydroxyethyldimethylammonium, piperazinium, N,N-dimethylpiperazinium, piperidinium, ethylenediammonium and choline).

Cyclodextrin complexes may be formed, for example, with α-, β- or γ-cyclodextrin, although complexes with β-cyclodextrin are generally preferred.

The heterocyclic amino group Y may for example have a 5,6 or 7-membered ring, e.g. pyrrolidino, piperidino, morpholino, piperazino, thiomorpholino, 1,1-dioxothiomorpholino, homomorpholino and hexamethyleneimino. The carbon atoms of the heterocyclic rings may be substituted, for example, by a methyl, ethyl or butyl group. Examples of the optional substituent $R^{3a}$ which may be present on the second nitrogen atom in the ring are methyl, ethyl, butyl, benzyl and phenethyl. In particular, the group Y may represent a saturated heterocyclic amino group which has 5,6 or 7 ring members and optionally contains in the ring —O—.

In general, Y is preferably pyrrolido, piperidino or hexamethyleneimino, optionally substituted by one or two $C_{1-4}$ alkyl (particularly methyl) groups. Especially preferred Y groups are piperidino and hexamethyleneimino.

In general, $R^1$ is preferably a hydrogen atom.

When n is 1, $-(CH_2)_m-$ is in particular $-(CH_2)_2-$ or $-(CH_2)_4-$, especially $-(CH_2)_2-$.

Alk may be, for example, a straight or branched $C_{1-3}$ alkyl chain (e.g. methylene, ethylene or propylene). Alk preferably represents methylene or propylene.

The group

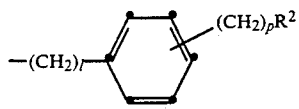

may be attached at the ortho, meta or para position of the phenyl group in the rest of the molecule. Preferably l represents zero and the group

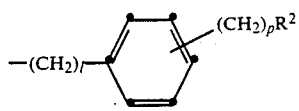

is preferably attached at the meta or, more preferably, the para position. The moiety p is preferably zero, 1 or 2.

Examples of the group $R^2$ include hydroxy, $CO_2R^3$, $-CONR^3R^4$, $-NHCOR_3$, $-NHSO_2R_5$, $-SO_2R_5$, $-SO_2NR^3R^4$, $-NR^3R^4$ and $-NHCONR^3R^4$.

When $R^3$ or $R^4$ is a $C_{1-4}$ alkyl group the $C_{1-4}$ alkyl group may be straight or branched and may be, for example, methyl, ethyl, n-propyl, i-propyl, n-butyl and t-butyl. When $R^3$ or $R^4$ is a $C_{7-10}$ aralkyl group it may be, for example, benzyl or phenethyl. $R^3$ and $R^4$ preferably independently represent hydrogen atoms or methyl groups. Examples of the group $R^5$ include methyl, ethyl, n-propyl, i-propyl, n-butyl and t-butyl. $R^5$ preferably represents a methyl group.

A particular group of compounds of formula (1) are those of formula (1C)

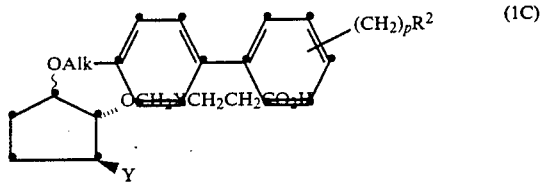

and the physiologically acceptable salts, solvates and cyclodextrin complexes thereof, wherein X is cis or trans $-CH=CH$ or $-CH_2CH_2-$, Y is a saturated heterocyclic amino group which has 5, 6 or 7 ring members and optionally contains in the ring —O—, Alk is a straight $C_{1-3}$ alkyl chain, p is zero, 1 or 2 and $R^2$ is as previously defined. Preferred compounds of formula (1C) are those in which $R^2$ represents $-OH$, $-CO_2H$, $-CONH_2$, $-NHCOCH_3$, $-NHSO_2CH_3$, $-SO_2NHCH_3$, $-NHCONH_2$ or $-SO_2CH_3$. Compounds of formula (1C) in which the group $-(CH_2)_pR^2$ is attached at the ortho position of the phenyl group in the rest of the molecule are particularly preferred.

In general preferred compounds of formula (1A) are those in which the carbon atom carrying the α-side chain (i.e. the $-O(CH_2)_nX(CH_2)_mCO_2R^1$ group) is in the R configuration L(and mixtures containing this isomer).

A particularly preferred compound of the invention is:

[1α(Z), 2β, 5β]-(±)-6-[[2-(hexahydro-1H-azepin-1l-yl)-5-[[2'-(hydroxymethyl)[1,1'-biphenyl]-4-yl]methoxy]cyclopentyl]oxy]-4-hexenoic acid (hereinafter referred to as 'Compound A'), and its physiologically acceptable salts, solvates and cyclodextrin (e.g. β-cyclodextrin) complexes.

Another particularly preferred compound of the invention is the 1R isomer of Compound A, namely [1R-[1α(Z),2β,5β]]-6-[[2-(hexahydro-1H-azepin-1-yl)-5-[[2'-(hydroxymethyl)[1,1'-biphenyl]-4-yl]methoxy]cyclopentyl]oxy]-4-hexenoic acid, and its physiologically acceptable salts, solvates and cyclodextrin (e.g. β-cyclodextrin) complexes.

A further particularly preferred compound of the invention is the isomer of Compound A, namely [1S-[1α(Z),2β,5β]]-6-[[2-(hexahydro-1H-azepin -1-yl)-5-[[2'-(hydroxymethyl)[1,1'-biphenyl]-4-yl]methoxy]cyclopentyl]oxy]-4-hexenoic acid, and its physiologically acceptable salts, solvates and cyclodextrin (e.g. β-cyclodextrin) complexes.

Compounds of formula (1) have excellent endoperoxide and thromboxane antagonist activity and consequently inhibit blood platelet aggregation, bronchoconstriction and vasoconstriction. A test to determine inhibition of blood platelet aggregation is as described by Lumley and Humphrey (*J. Pharmacol. Methods*, 1981, 6, 153–166) using collagen of [1R-[1α,4α,5β(Z), 6α(-1E,3S*)]]-7-[6-(3-hydroxy-1-octenyl)-2-oxabicyclo[2.2.1]hept-5-yl]-5-heptenoic acid (U-46619) as the pro-aggregatory agent.

The ability of the compounds of the invention to inhibit vasoconstriction or bronchoconstriction is determined using the relevant isolated tissue (e.g. spirally cut rat aortic strip or guinea-pig lung parenchymal strip) by measuring the effect of the compound to be tested on the contraction of the tissue to U-46619.

The present compounds are thus of interest for use in human and animal medicine, more particularly for use in the treatment or prophylaxis of conditions mediated by thromboxane $A_2$. the compounds of formula (1) may find particular use in the treatment and prophylaxis of occlusive vascular disease, including myocardial infarction, cardiac fatalities, unstable angina, transient ischaemic attacks and cerebral infarction, atherosclerosis and vessel wall disease, peripheral vascular disease, nephropathy, retinopathy, postoperative thrombosis and pulmonary embolism. The compounds are also of interest for use in renal dialysis and cyclosporin A-induced nephrotoxicity. In addition, the compounds of the invention are useful in the prophylaxis of peri- and postoperative complications following organ transplantation (particularly cardiac and renal), coronary artery bypass, peripheral artery bypass, angioplasty, thrombolysis and endarterectomy.

The compounds are also of potential use in the treatment of adult respiratory distress syndrome and the prevention of relapse of healed peptic ulcers.

The compounds may be formulated in a conventional manner for use with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by injection or continuous infusion. Formulations for injections may be presented in unit dosage form in ampoules, or in multi-dose containers, with an added preservative. The compositions may take such forms as suspensions, solutions or emulsions in oil or aqueous vehicles; and may contain formulatory agents such as suspending, stabilizing and/or dispersing agents. Alternatively, the active ingredient may be in powder form for reconstitution before use with a suitable vehicle e.g. sterile pyrogen-free water.

For administration by inhalation the compounds are conveniently delivered in the form of an aerosol spray presentation from pressurized packs or a nebulizer, or as cartridge from which the powdered composition may be inhaled with the aid of a suitable device. In the case of a pressurized aerosol the dosage unit may be determined by providing a valve to deliver a metered amount.

The precise dose administered will of course depend on the age and condition of the patient, the specific condition to be treated and the mode of administration.

However, generally, for use as antithrombotic agents, the compounds are preferably administered orally, for example in amounts of 0.05 to 10 mg/kg body weight, 1 to 4 times daily.

The compounds of the invention may, if desired, be administered in combination with one or more other therapeutic agents such as a thromboxane synthase inhibitor.

Suitable methods for preparing compounds of formula (1) are described below, the terms $R^1$, $R^2$, X, Alk, Y, l, m, n and p being as defined above except where otherwise indicated. It will be appreciated that the following reactions may require the use of, or conveniently may be applied to, starting materials having protected functional groups, and deprotection might thus be required as a final step to yield a compound of the invention. Protection and deprotection of functional groups may be effected using conventional techniques. Thus, for example, amino groups may be protected by acylation, subsequent descylation being effected when desired by hydrolysis using for example an acid such as hydrochloric acid or a base (e.g. aqueous sodium hydroxide). Hydroxyl groups may be protected using conventional hydroxyl protecting groups, for example as described in 'Protective Groups in Organic Chemistry', Ed. J. F. W. McOmie (Plenum Press, 1973) or 'Protective Groups in Organic Synthesis', by Theodora W. Greene (John Wiley and Sons, 1981). Examples of suitable protecting groups include heterocyclic groups such as tetrahydropyranyl which may be removed by hydrolysis under acidic conditions.

According to a process (A) compounds of formula (1) may be prepared by reacting corresponding compounds of formula (2)

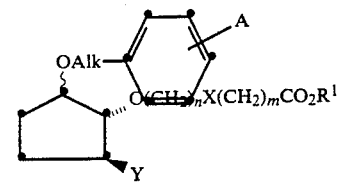
(2)

(where A is a displaceable atom or group) or salts thereof to replace the moiety A with the group

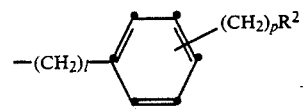

Displaceable atoms or groups represented by the moiety A include any conventional leaving group such as halogen (e.g. chlorine, bromine or iodine), triflate or a phosphate ester (e.g. diethylphosphate).

Replacement of the moiety A by a group

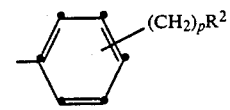

to provide a compound of formula (1) in which l is zero may be effected by a coupling reaction of a compound of formula (2) or a salt thereof with a compound of formula (3)

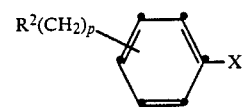
(3)

[where X is an atom or group as defined above for A or X is a group $-B(OH)_2$ or X is a suitable metal atom or metal-containing group such as Li, Cu, MgHal, ZnHal or $SnR'_3$ or X is a group $SiR'_3$ (wherein Hal is a halogen atom, e.g. chlorine, bromine or iodine, and $R^1$ is a $C_{1-6}$alkyl group, e.g. methyl or n-butyl, or an aryl group, e.g. phenyl)]. It will be understood that when X represents MgHal or Li the moiety $R^1$ may not represent methyl.

In a particular embodiment of process (A) compounds of formulae (2) and (3) are reacted wherein A represents a halogen atom (e.g. bromine) and X represents a group $-B(OH)_2$. The coupling reaction may conveniently be carried out in the presence of a suitable transition metal catalyst such as a palladium (O) or palladium (II) catalyst, for example $PdL_4$ or $PdCl_2L_2$ (where L is a phosphine ligand such as triphenylphosphine or tritolylphosphine) in a suitable solvent such as an ether (e.g. 1,2-dimethoxyethane or tetrahydrofuran), a hydrocarbon, for example an aromatic hydrocarbon (e.g. benzene), or a dipolar aprotic solvent such as N,N-dimethylformamide containing an appropriate base which may be, for example, a carbonate, bicarbonate or hydroxide of an alkali or alkaline earth metal (e.g. aqueous sodium carbonate) or a suitable amine such as a tertiary amine (e.g. triethylamine). the reaction may be effected at any suitable temperature up to and including reflux, for example in the range 20°-120° C. and preferably in the range 60°–80° C. Ultrasonic techniques or microwave may also be used to facilitate the reaction. The coupling reaction is preferably carried out in the presence of the catalyst (Ph$_3$P)$_4$Pd.

When A and X in formulae (2) and (3) are conventional leaving groups as defined for A in formula (2l) the coupling reaction may be carried out in a single step in the presence of a suitable transition metal catalyst (e.g. a palladium or nickel catalyst) and under reducing conditions (e.g. using a reducing agent such as zinc metal or hydrazine or by electrolytic reduction). suitable palladium catalysts include palladium-on-charcoal, a palladium (II) chloride-mercury (II) chloride couple, PdL$_4$ and PdCl$_2$L$_2$ (where L is as defined above). Suitable nickel catalysts include nickel (II) chloride and NiCl$_2$L$_2$ (where L is as defined above). the specific conditions for effecting the desired conversion will, of course, depend on the particular values of A and X in formulae (2) and (3) respectively. However, the conditions referred to in the following publications may be suitable for present purposes: Chem, Letters 1986, p. 407; J. Org. Chem. 1986, p. 2627; Tetrahedron Letters 1977, p. 4089; Synthesis 1978, p. 537; Bull. Chem. Soc. Japan 1980, 53, p. 1767 and Tetrahedron Letters 1985, p. 1655.

When X in formula (3) is a conventional leaving group as defined for A in formula (2), the compound of formula (2) may first be converted to a compound of formula (2a)

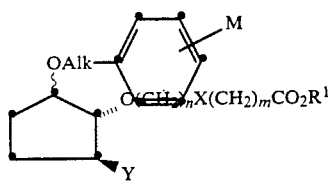

[where M is a suitable atom or metal-containing group such as Li, Cu, MgHal, ZnHal, HgHal or SnR'$_3$ or X is a group SiR'$_3$ (wherein Hal and R' are as previously defined)] and then the compound of formula (2a) reacted with an appropriate compound of formula (3) to give the desired product. It is to be understood that when M represents MgHal or Li then the moiety R$^1$ in formula (2al) may not represent a methyl group.

Compounds of formula (2al) may be prepared by treating a compound of formula (2) in which A represents a conventional leaving group such as halogen (e.g. chlorine or, more especially, bromine or iodine), triflate or a phosphate ester (e.g. diethylphosphate) with a reagent capable of introducing the moiety M. Suitable reagents and conditions for effecting the desired conversion are known in the art (cf. J. Am. Chem. Soc. 1987, p. 8056; J. Org. Chem, 1984, lp. 5280; Chem. Letters 1981, p. 829; J. Organometal, Chem, 1983, p. 551; Tetrahedron Letters 1987, p. 4715 and Tetrahedron Letter 1983, p. 4895l). Thus, for example, a compound of formula (2a) in which M is ZnHal may be prepared from a corresponding halo compound of formula (2) in which A is a halogen atom (e.g. bromine or iodine) by reaction with activated zinc. A compound of formula (2a) in which M is Cu may be prepared from a corresponding halo compound of formula (2) in which A is a halogen atom (e.g. bromine or iodine) by reaction with Riecke copper. A compound of formula (2a) in which M is MgHal may be prepared from a corresponding halo compound of formula (2) in which A is a halogen atom (e.g. bromine or iodine) by reaction with magnesium or with MgHal$_2$ (where Hal is as defined above) in the presence of lithium. A compound of formula (2a) in which M is Li may be prepared from a corresponding halo compound of formula (2) in which A is a halogen atom (e.g. bromine or iodine) by reaction with a suitable organolithium reagent (e.g. n-butyllithium). A compound of formula (2a) in which M is SnR'$_3$ or SiR'$_3$ may be prepared from a corresponding compound of formula (2) in which A is a conventional leaving group such as a halogen atom (e.g. bromine or iodine), triflate or a phosphate ester (e.g. diethylphosphate) by reaction with either R$_3$'Sn-SnR'$_3$ or R'$_3$Si-SiR'$_3$ in the presence of a suitable palladium catalyst. Alternatively, Al(-SiR'$_3$)$_3$ and a catalyst NiCl$_2$L$_2$ (where R' and L are as defined above) may be used to prepare a compound of formula (2a) in which M is SiR'$_3$.

The resulting compound of formula (2a) is then treated with a compound of formula (3) in which X is a conventional leaving group such as halogen (e.g. bromine or iodine), triflate or a phosphate ester (e.g. diethylphosphate). The coupling reaction may conveniently be effected in the presence of a suitable transition metal catalyst such as a palladium or nickel catalyst (e.g. PdL$_4$, PdCl$_2$L$_2$, NiCl$_2$ or NiCl$_2$L$_2$, where L is as defined previously) in a suitable solvent such as an ether (e.g. diethyl ether, tetrahydrofuran or 1,2-dimethoxyethane), hexamethylphosphoramide, dimethylformamide, dioxane, acetonitrile or an aromatic hydrocarbon (e.g. benzene). The specific conditions for effecting the desired reaction will, of course, depend on the particular values of M and X in formulae (2a) and (3) respectively. However, the conditions referred to in the following publications may be suitable for present purposes: Comprehensive Organometal, Chem. volume 8, p. 910; Current Trends in Organic Synthesis (Pergamon Press 1982) p. 269; J. Am. Chem. Soc. 1941, 63, p. 2316; J. Organometal, Chem. 1984, 267, Cl; J. Am. Chem. Soc. 1987, 109, p. 5479; J. Org. Chem. 1983, p. 1333; Tetrahedron Letters 1986, p. 4407; J. Am. chem. Soc, 19789, 101, p. 4992 and J. Organometal, Chem. 1983, 250, p. 551.

When X in formula (3l) is a metal or metal-containing group as defined previously, the coupling reaction may be carried out with a compound of formula (2) in which A is a conventional leaving group as defined above in a single step using the conditions described above for the coupling of compounds of formulae (2al) and (3).

It is to be understood that the use of stoichiometric amounts of the transition metal "catalyst" may be advantageous in some of the aforementioned coupling reactions.

Intermediates of formula (3) are either known compounds or can be prepared from known compounds using methods analogous to those used to prepare the known compounds of formula (3).

The intermediates of formula (3) in which X is a group —B(OH)$_2$ are either known compounds or may be prepared by methods described by W. J. Thompson et. al. in *J. Org. Chem.*, 1984, 49, 5237.

The boronic acids of formula (3) may be formed in situ under the conditions of the coupling reaction described hereinbefore using the corresponding anhydrides of formula (4) or (4a) which are known classes of compounds described by H. R. Snyder et. al in *J. Amer. Chem. Soc.*, 1958, 80, 3611 and F. R. Bean et. al. in *J. Amer. Chem. Soc.*, 1932, 54, 4415.

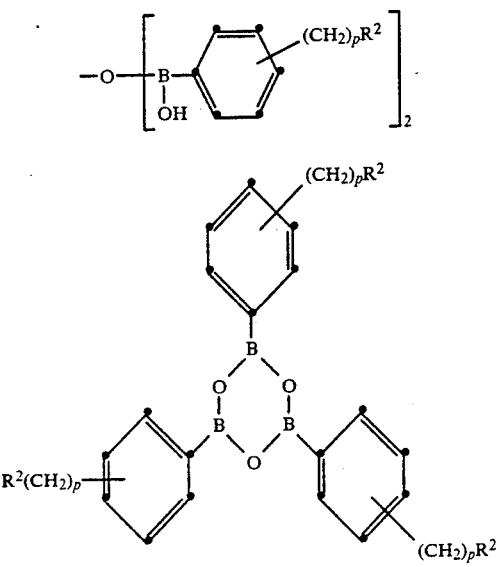

The boronic acid of formula (3) where —(CH$_2$)$_p$R$^2$ is 2—CH$_2$OH is formed in situ from the known cyclic ester of formula (5)

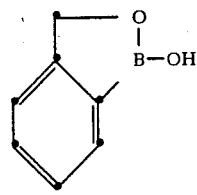

Where suitable, the group R$^2$ may be protected before the preparation of the corresponding boronic acid (3). Thus, for example, a hydroxyl group may be protected as a silyl ether e.g. as a t-butyldimethyl silyl ether.

In a further embodiment, compounds of formula (1) in which R$^1$ is a methyl group and l is 1 may be prepared by reacting a compound of formula (2) (where A is a displaceable atom or group as previously defined and R$^1$ is a methyl group) with a suitable organometallic reagent such as a tin containing reagent of formula (6)

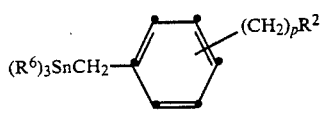

(where R$^6$ is a C$_{1-4}$ alkyl group such as n-butyl) or a zinc containing reagent of formula (7)

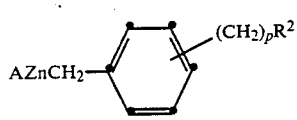

(where A is a halogen atom, e.g. bromine) in the presence of transition metal catalyst such as (Ph$_3$P)$_4$Pd, or a pre-reduced nickel acetylacetonate —Ph$_3$P complex in a suitable solvent such as an ether (e.g. tetrahydrofuran), [(CH$_3$I)$_2$N]$_3$PO or a mixture of these, at a suitable temperature, preferably ambient temperature.

The organometallic reagents used in the above processes are either known compounds or may be prepared by analogous methods to those used for the preparation of the known compounds. Where suitable the group R$^2$ may be protected, e.g. before the preparation of the organometallic reagents (6) and (7).

In a further process (B) the compounds of formula (1) in which R$^1$ is a hydrogen atom and l is zero may be prepared by reacting a boronic acid derivative of formula (8)

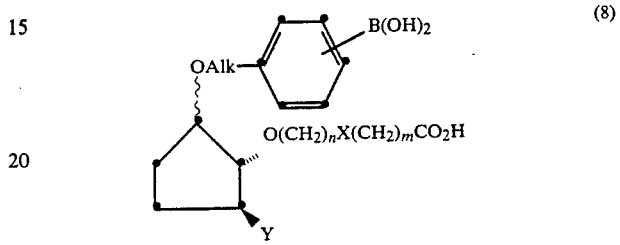

with a halobenzene of formula (9)

(where A is a halogen atom, e.g. bromine) under the conditions described in process (A) above for the reaction between a compound of formula (2) in which A is a halogen atom, e.g. bromine, and a compound of formula (3l) in which X is a group —B(OH)$_2$.

The intermediates of formula (8) may be prepared by reaction of halobenzenes of formula (2) where R$^1$ is a hydrogen atom with an organolithium reagent such as n-butyl lithium in a solvent such as an ether (e.g. tetrahydrofuran) at low temperature (e.g. —100° to —70° C.) and a boron reagent such as tri-isopropylborate.

The above conditions may yield the desired boronic acid or the corresponding boronic acid anhydride. If the anhydride is prepared then this compound may be used in the coupling reaction; the corresponding boronic acid may then be formed in situ under the conditions of the coupling reaction.

The intermediates of formula L(9) are either known compounds or may be prepared by methods used for the preparation of the known compounds of formula (9).

In another process (C) compounds of formula (1) in which X is —CH═CH— may be prepared by reacting a compound of formula (10)

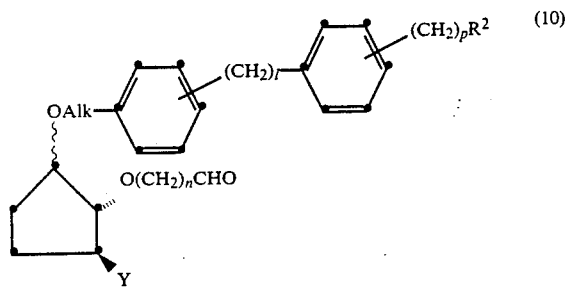

with an appropriate Wittig reagent, e.g. a phosphorane of formula $R^7_3P=CH(CH_2)_mCO_2R^1$ (where $R^1$ is $C_{1-6}$ alkyl or aryl, e.g. monocyclic aryl such as phenyl) or a salt thereof, e.g. the potassium salt. Suitable reaction solvents include hydrocarbons (e.g. benzene and toluene), ethers (e.g. tetrahydrofuran) and dialkylsulphoxides (e.g. dimethylsulphoxide). The reaction may be carried out at any suitable temperature from $-70°$ to $50°$ C., preferably at room temperature. The reaction is particularly suitable for the preparation of compounds in which $R^1$ is a hydrogen atom.

In a further process (D) compounds of formula (1) may be prepared by alkylation of a n alkoxide (e.g. an alkali metal alkoxide) derived from an alcohol of formula (11)

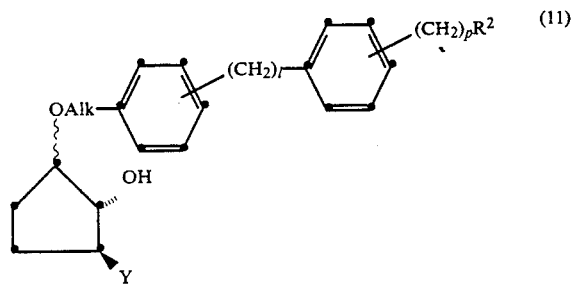

with an alkylating agent $L(CH_2)_nX(CH_2)_mCO2R^8$ (where L is a leaving group such as a halogen atom e.g. chlorine bromine or iodine, or a hydrocarbylsulphonyloxy group, e.g. methanesulphonyloxy or p-toluenesulphonyloxy and $R^8$ is a methyl group or preferably a suitable acid protecting group e.g. tertiary butyl). Suitable bases for the preparation of the alkoxide include for example sodium hydride. The alkoxide may be formed in a solvent (e.g. a substituted amide such as dimethylformamide) at a suitable temperature from ambient to 100° C. the alkylating agent is then added to the cooled (e.g. 0° C.) solution of the alkoxide. The protecting group may be removed by hydrolysis for example as described in process (E) below.

The alkylating agents $L(CH_2)nX(CH_2mCO_2R^8$ are either known compounds or may be prepared by methods analogous to those used for the preparation of the known compounds.

Intermediates of formula (11) may be prepared from compounds of formula (12)

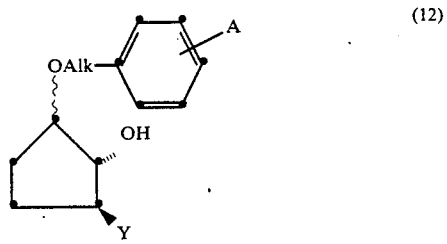

(where A is as defined previously) according to the method of process (A) above.

Intermediates of formula (2) may also be prepared from intermediates of formula (12) according to the method of process (D) above.

Intermediates of formula (10l) may be prepared by reacting an acetal of formula (13)

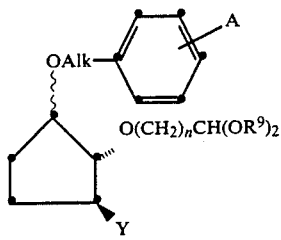

(where $R^9$ is a $C_{1-4}$ alkyl, e.g. methyl, group or $CH(OR^9)_2$ forms a 1,3-dioxolane or 1,3-dioxane ring and A is as defined previously) according to the method of process (A) above, followed by hydrolysis to give the aldehydes (10) for example using hydrochloric acid in a suitable solvent (e.g. acetone).

The intermediate acetals of formula (13) may be prepared by alkylation of a corresponding alcohols of formula (12) using an alkylating agent $L(CH_2)_nCH(OR^{9l})_2$ under the conditions previously described in process (D) above.

The intermediate alcohols of formula (12l) may be prepared from the epoxy-ethers of formula (14) or (15)

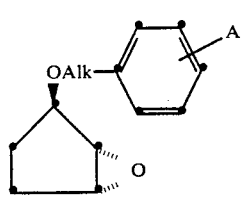

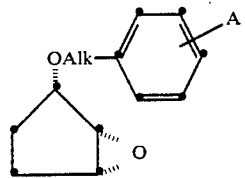

by reaction with an amine YH in the absence or presence of a solvent e.g. butanol at suitable temperatures up to reflux.

The epoxy-ethers of formula (14) may be prepared by epoxidation of ethers of formula (16)

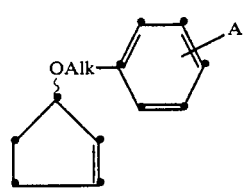

using a per-acid such as m-chloroperbenzoic acid in a solvent such as dichloromethane.

The ethers of formula (16l) may be obtained by alkylation involving (i) an alcohol of formula (17) and a compound

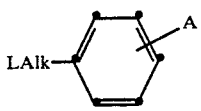

(where L is as previously defined) or (ii) a compound of formula (18) and an alcohol

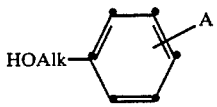

(17)

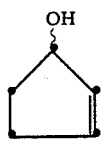

(18)

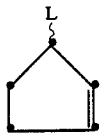

(where L is as previously defined). The alkylation reaction may be carried out in the presence of a base (e.g. sodium hydroxide) and a quaternary alkyl ammonium salt e.g. tetrabutylammonium hydrogensulphate, or under the conditions described in process (D) above.

The epoxy-ethers of formula (15) may be prepared by alkylation of the alcohol (19)

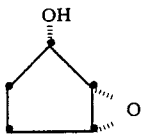

(19)

with a compound

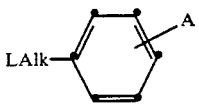

(where L is as previously defined) under the conditions described just above.

The intermediates of formulae (17), (18) and (19) are either known compounds or may be prepared by methods analogous to those used for the preparation of the known compounds of formulae (17), (18) and (19).

Processes (E)-(H) below describe methods for the preparation of compounds of formula (1) by interconversion or simple derivatisation.

(E) Compounds of formula (1) containing a group —COOH may be prepared by hydrolysis of a corresponding ester (e.g. a $C_{1-6}$ alkyl ester such as a methyl or t-butyl ester) for example using a base such as sodium hydroxide or potassium hydroxide in a suitable solvent (e.g. an alcohol such as methanol or ethanol) at a suitable temperature up to reflux.

(F) Compounds in which $R^1$ is a methyl group may be prepared by esterification of the corresponding carboxylic acid. Conventional esterification techniques may be used, for example by reaction with methanol in the presence of a mineral acid such as hydrochloric acid or sulfuric acid.

(G) Compounds of formula (1) in which X is trans —CH=CH— may be prepared by isomerizing the corresponding cis compound. The isomerization may for example by effected by treatment with p-toluenesulphinic acid in dioxan (e.g. at reflux) or azobisisobutyronitrile and thiophenol, using for example a hydrocarbon solvent (e.g. benzene) and any suitable temperature up to reflux.

(H) Compounds of formula (1) in which X is a —CH$_2$CH$_2$— group may be prepared by reduction of the corresponding compound in which X is a cis or trans —CH=CH— group. Suitable methods of reduction include hydrogen in the presence of a suitable catalyst such as palladium on a support (e.g. carbon). suitable solvents include alcohols (e.g. methanol or ethanol) and esters (e.g. ethyl acetate).

(I) Where salts of compounds of formula (1) are desired such salts may be formed in conventional methods, for example by treatment with an acid or with a base. Salt formation may be effected, for example, in a suitable solvent such as an ether (e.g. diethylether), a nitrile (e.g. acetonitrile), a ketone (e.g. acetone), a halogenated hydrocarbon (e.g. chloroform or dichloromethane), an ester (e.g. ethyl acetate or isopropyl acetate) or an alcohol (e.g. methanol, ethanol or isopropanol). Salts may also formed by conversion of one salt of a compound f the invention into another, e.g. by ion exchange using conventional methods.

Intermediate compounds of formulae (12), (131), (14), (15) or (16) may be converted to the corresponding intermediates containing the group

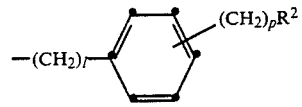

by the methods of process (A) above or via intermediate boronic acids by the method of process (B) above.

Intermediates of formulae (2), (2a), (8), (10), (11), (12), (13), (14), (15) and (16) and the anhydride precursors of the boronic acids of formula (8) are novel compounds and form a further aspect of the present invention. The compounds of formulae (2) and (8) and the corresponding aforementioned anhydrides are particularly useful intermediates.

When a specific enantiomer of formula (1) is required, starting materials having the desired stereochemical configuration should be used in the above processes. For example, individual enantiomers of the alcohol of formula (17) may be obtained from the corresponding racemic alcohol, using methods such as those described by V. S. Martin et. al. in *J. Amer. Chem. Soc.*, 1981, 103, 6237. Alternatively, the enantiomers of an alcohol of formula (12) may be prepared from the corresponding racemic alcohol using for example a suitable chiral resolving agent such as resolved 1-(1-naphthyl)ethylisocyanate as described by W. H. Pirkle and M. S. Hoekstra in *J. Org. Chem.*, 1974, 39, 3904 or using resolved dibenzoyl tartaric acid under conventional conditions. Thus, for example, the desired enantiomers may be prepared by treating the racemic alcohol (121) with (D) or (L)-dibenzoyl tartaric acid as appropriate in a suitable solvent such as an alcohol (e.g. methanol) or a carboxylic acid ester (e.g. ethyl acetate) or a mixture of such solvents with heating (e.g. at reflux).

Cyclodextrin complexes of compounds of formula (1) may be prepared from a compound of formula (1) or a salt (e.g. the hydrochloride salt) thereof by dissolving the compound of formula (1) or a salt thereof in water or an organic solvent which is miscible with water (e.g. an alcohol such as methanol) and adding to the solution as a solution of α-, β- or γ-cyclodextrin (or a hydrate thereof) or a mixture of two or three of them together in water and/or an organic solvent which is miscible with water. The reaction may conveniently take place at any temperature in the range from 0° to 80° C. However, the mixture is preferably kept at room temperature and the desired complex obtained by concentrating the mixture under reduced pressure or by allowing the mixture to cool.

It will be appreciated by persons skilled in the art that solvates (e.g. hydrates) of the compounds of the invention may be formed during the work-up procedure in the final step conversion reaction to form the appropriate compound of the invention.

The following examples illustrate the invention. Temperatures are in ° C. Flash column chromatography (F.C.C.) and thin layer chromatography (t.l.c.) were carried out using the following systems:
A) Silica.
B) Triethylamine deactivated silica. Dried refers to drying with MgSO$_4$. NaH refers to a dispersion of sodium hydride in oil. The following abbreviations are used.

EA - ethyl acetate
ER - diethyl ether
DMF - dimethylformamide
THF - tetrahydrofuran
PE - petroleum ether (b.p. 40°–60°)
NH$_3$ - 0.880 ammonia
DCM - dichloromethane
TTP - tetrakis(triphenylphosphine)palladium (O)

INTERMEDIATE 1

1,1-Dimethylethyl 2-bromobenzeneacetate

A mixture of 2-bromophenylacetic acid (5.02 g), N,N-dicyclohexylcarbodiimide (5.3 g), 4-pyrrolidinopyridine (0.4 g) and t-butanol (1.74 g) in DCM (120 ml) was stirred at room temperature, under nitrogen, for 4 h. The mixture was left to stand for 18 h, then ER (150 ml) was added and the mixture was filtered and washed with ER. The filtrate was evaporated in vacuo to leave a yellow suspension. F.C.C. (A) eluting with hexane gave a white semisolid, which was further chromatographed eluting with hexane, then 1% ER in hexane, and finally 2% gave a colorless liquid. Vacuum distillation by Kugelrohr at 0.4 mmHg and at 140°–150° gave the title compound as a colorless oil (0.55 g). T.l.c. (A) hexane:ER (3:1) Rf 0.68.

INTERMEDIATE 2

[2-[(Methylsulphonyl)methyl]phenyl]boronic acid

A solution in DMF (2.0 ml) of [2-(bromomethyl)-phenyl]boronic acid (399 mg) was added in one portion to a stirred slurry of sodium methanesulphinate (200 mg) in DMF (2.0 ml). The mixture was stirred for 2.5 h i nd then poured into 1M hydrochloric acid (100 ml) and extracted with EA (3×50 ml). the combined extracts were dried and evaporated. On standing a solid material precipitated, which was washed with ER to give white crystals of the title compound (115 mg), m.p. 133°–137°. T.l.c. (A) ER:hexane (3:2) Rf 0.51.

INTERMEDIATE 3

Sodium 2l-bromobenzenemethanesulphonate

2-Bromobenzyl bromide (120 g) was added to a warm (40° internal), vigorously stirred, partial solution of sodium sulfite (5.05 g) in water (15 ml). The temperature was raised to 80° over 1 h and kept at that temperature for 3 h. Ethanol (15 ml) was added and the mixture slowly cooled to room temperature. The solid was filtered off, washed with aqueous ethanol (1:1; 5 ml) and ER (3'20 ml) and dried in vacuo to give the title compound (8.77 g) as white plates, m.p. 286°–8° (dec).

INTERMEDIATE 4

2-Bromo-N-methylbenzenemethanesulphonamide

A mixture of Intermediate 3 (1.5 g), phosphoryl chloride (1.7 g), DMF (0.25 ml) and DCM (10 ml) was stirred under reflux for 23 h. The cooled reaction mixture was added, over 5 min, to a vigorously stirred mixture of ice and water (50 ml). After 45 min, the separated aqueous layer was extracted with DCM (15 ml). The combined DCM solutions were washed with water (20 ) then added, over 30 min, to vigorously stirred, ice cooled aqueous methylamine (20 ml of 40% aqueous solution + 10 ml water). After 1 h, the mixture was diluted with water (25 ml) and the aqueous layer extracted with DCM (2×20 ml). The dried extracts were evaporated in vacuo to leave a colorless oil, which crystallized on standing. Crystallization from EA-hexane gave the title compound (0.6 g) as white crystals, m.p. 72.5°–74°. T.l.c. (A) ER Rf 0.46.

INTERMEDIATE 5

(A)-1,1-Dimethylethyl 6l-chloro-4l-hexenoate n-Butyl lithium (1.6M; 6 ml) was added over 5 min, under nitrogen, to a stirred, cooled (−10°) solution of cyclohexyl isopropyl amine (1.64 ml) in dry THF (10 ml). After 5 min the solution was cooled to −78° and after a further 15 min., t-butyl acetate (1.35 ml) was added over 5 min. After 20 min., cis-1,4-dichloro-2-butene (4 ml) was added and the mixture allowed to warm to 10° over 4 h. The mixture was diluted with hydrochloric acid (1N; 25 ml) and extracted with ER (2×30 ml). The extracts were washed with hydrochloric acid (1N; 20 ml), brine (20 ml) and sodium bicarbonate (8%; 20 ml), dried and evaporated in vacuo to leave a pale yellow oil. The excess dichlorobutene was removed on the Kugelrohr (90°/13 mml) to leave a yellow oil. F.C.C. (A) eluting with light petroleum (40°–60°), increasing to DCM in petrol and finally DCM, gave the title compound (0.66 g) as a colorless liquid. T.l.c. (A) DCM Rf 0.48.

INTERMEDIATE 6

(±)-1-Bromo-4-[[(2-cyclopenten-1l-yl)oxy]propyl]benzene

4l-Bromobenzenepropanol[1] (0.93 g) was dissolved in dry DMF (4 ml) and treated with sodium hydride (460 mg, 80%). The mixture was, after complete reaction, cooled to 0° and 3l-chloro-1-cyclopentene (1.5 ml) was added slowly dropwise, with stirring. The mixture was stirred at 0° for 1 h and then left to stand overnight. A mixture of brine (25 ml) and 20% potassium carbonate solution (25 ml) was added and the product was extracted with EA (3×30 ml ). The combined extracts were dried and evaporated to give an orange oil. F.C.C. (A) eluting with hexane:ER (19:1) gave the title compound (406 mg) as a pale yellow oil. T.l.c. (A) hexane-ER (19:1) Rf 0.27. 1. K. Hanada et. al., Jpn. Kokai Tokyo Koho 79, 141, 735 November 1979.

INTERMEDIATE 7

(±)-1-Bromo-4-[[(2-cyclopenten-1-yl)oxy]methyl]benzene

A mixture of the 2-cyclopenten-1ol[2] (6 g), tetrabutylammonium hydrogensulphate (1 g), 4l-bromobenzyl bromide (23 g) in DCM (100 ml) and 70l% sodium hydroxide solution (40 ml) was stirred at 20° for 3 days. A further quantity (7.5 g) of the bromide was added and stirring continued for a further 24 h. The mixture was diluted with water and DCM and the layers were separated. The aqueous layer was extracted with DCM and the organic extracts were washed with water, dried and evaporated to give an oil which was purified by F.C.C. (A) eluting initially with PE then with 19:1 PE-ER to give the title compound as a pale-yellow oil (14.1 g).
  Anaylsis Found: C,56.7; H,5.0.
  $C_{12}H_{13}BrO$ requires C,56.9; H,5.2%.
2. J. L. Eisch et. al., J. Org. Chem. 44, 587 (1979)
In a similar manner was prepared Intermediate 8.

INTERMEDIATE 8

(1α,2β,5α)-(±)-2-[(4-Bromophenyl)methoxy]-6-oxabicyclo[3.1.0]hexane (6.93 g)

Analysis Found: C,53.9; H,5.0.
$C_{12}H_{13}BrO$ requires C,53.55; H,4.9%.
From l(1α,2β,6α)-6-oxabicyclo[3.1.0]hexan-2-ol (3 g), 4-bromobenzylbromide (9 g), tetrabutylammonium hydrogensulphate (0.3 g), DCM (60 ml) and 70l% w/v sodium hydroxide solution except that F.C.C. (A) was carried out using PE then ER-PE (1:1) as eluent.

INTERMEDIATE 9

(±)-1-Bromo-3-[[-2-(cyclopenten-1-yl)oxy]methyl]benzene

A solution of 2-cyclopenten-1-ol (8.7 g), 3l-bromobenzylbromide (25.8 g) and tetrabutylammonium hydrogensulphate (3.7 g) in toluene (150 ml) were treated with 17M sodium hydroxide (75 ml) and stirred vigorously for 4.5 h, then treated with water (150 ml). the toluene layer was separated and the aqueous layer extracted with ER (3×50 ml). The combined organic phases were dried and evaporated to give a yellow oil. F.C.C. (A) eluting with hexane then hexane:ER (9:1) to give the title compound as a colorless oil (18.3 g). T.l.c. (A) hexane Rf 0.16.

INTERMEDIATE 10

(1α,2α,5α)-(±)-2-[(4-Bromophenyl)methoxy[-6-oxabicyclo[3.1.0]hexane m-Chloroperbenzoic acid (85%, 13.4 g) was added over 1.5 h to a cold (0°) stirred solution of Intermediate 7 in DCM (200 ml). The mixture was stirred at ambient temperature for 16 h, filtered and the filtrate washed with a solution of potassium carbonate (150 g) and sodium sulfite (50 g) in water (500 ml). The aqueous layer was extracted with DCM and the combined organic extracts were dried and evaporated. The residue was purified by F.C.C. (A) using PE-ER (3:1) as eluent to give the title compound as an oil (5.64 g).
  Analysis Found: C,53.32; H,4.83.
  $C_{12}H_{13}BrO_2$ requires C,53.55; H,4.87%.
In a similar manner were prepared Intermediates 11 and 12.

INTERMEDIATE 11

(1α,2α,5α)-(±)-2-[(3-Bromophenyl)methoxy]-6-oxabicyclo[3.1.0]hexane (14.3 g

T.l.c. (A) hexane:ER (3:1) Rf 0.39.
From m-chloroperbenzoic acid (32.0 g) and Intermediate 9 (23 g) except that, after washing, the mixture was evaporated to give a colorless oil which was purified by F.C.C. (A) eluting with hexane, then hexane:ER mixtures (19:1), (9:1) and (4:1).

INTERMEDIATE 12

(1α,2α,5α)-(±)-2-[3-(4-Bromophenyl)propoxy]-6-oxabicyclo[3.1.0]hexane (1.47 g)

T.l.c. (A) hexane:EA (9:1l) Rf 0.36 and 0.40
From Intermediate 6 (5.8 g) and m-chloroperbenzoic acid (8.6 g) except that, after washing, the mixture was evaporated to leave a pale yellow oil which was purified by F.C.C. (A) eluting with hexane:EA (9:1), (18:3), and finally (4:1).

INTERMEDIATE 13

(1α,2β,5β)-(±)-2)[(4-Bromophenyl)methoxy]-5-(hexahydro-1H-azepin-1-yl)-cyclopentan-1-ol A solution of Intermediate 10 (5.43 g) and hexamethyleneimine (25 ml) in butan-1-ol (75 ml) were heated at reflux for 22.5 h. Evaporation of the solvent and excess hexamethyleneimine in vacuo gave a residue which was purified by F.C.C. (B) with EA:methanol (9:1) as the eluent to give the title compound as a pale brown oil (6.6 g).
  Analysis Found: C,59.0; H,7.3; N,4.15.
  $C_{18}H_{26}BrNO_2$ requires C,58.7; H,7.1; N,3.8%.
In a similar manner were prepared Intermediates 14–18.

INTERMEDIATE 14

[1α,2α,5β]-(±)-2-[(4 Bromophenyl)methoxy]-5-(hexahydro-1H-azepin-1-yl)cyclopentan-1ol (13.76 g).

T.l.c. (B) methanol:EA (1:10) Rf 0.4
From Intermediate 8 (11.35 mg) and hexamethyleneimine (14.5 ml) in butan-1-ol (65 ml) except that F.C.C. (B) was carried out with methanol:EA (1:20) as eluent.

INTERMEDIATE 15

[1α,2β,5β]-(±)-2-[(4-Bromophenyl)methoxy]-5-(4-morpholinyl)-1-cyclopentanol (5.06 g), m.p. 86°-88°

T.l.c. (A) EA Rf 0.1.
From Intermediate 10 (10.01 g) and morpholine (19 ml) in butan-1-ol (60 ml) except that F.C.C. (B) was carried out with 3% methanol in EA as eluent.

INTERMEDIATE 16

[1α,2β,5β]-(±)-[2-[(4-Bromophenyl)methoxy]-5-(1-piperidinyl)]-1-cyclopentanol (13.16 g)

T.l.c. (B) EA:methanol (9:1) Rf 0.35.
From Intermediate 10 (10 g) and piperidine (35 ml) in butan-1-ol (60 ml) except that F.C.C. (A) was used eluting with 31% methanol in EA, followed by 3% methanol and 0.5% triethylamine in EA, then 51% methanol and 0.5% triethylamine in EA.

Analysis Found: C,57,3; H,7,0; N,4.0.
$C_{17}H_{24}BrNO_2$ requires C,57.6; H,6.8; N,4.0%.

INTERMEDIATE 17

(1α,2β,5β)-(±)-2-[(3Bromophenyl)methoxy]-5-(hexahydro-1H-azepin-1-yl)-cyclopentan-1ol (16.8 g)

T.l.c. (B) hexane:ER (1:1)Rf 0.06.
Analysis Found: C,58.45; H,7.2; N,4.0
$C_{18}H_{26}BrNO_2$ requires C,58.7; H,7.1; N,3.8%.

From Intermediate 11 (12.25 g) and hexamethyleneimine (50 ml) in butan-1ol (50 ml) except that F.C.C. (B) was carried out with EA then EA:methanol (19:1) as eluent.

INTERMEDIATE 18

(1α,2β,5β)-(±)-2-[3-(4-Bromophenyl)propoxy]-5-(1-piperidinyl)-cyclopentan-1-ol (1.55 g T.l.c. (B) EA:methanol (9:1) Rf 0.5.

From Intermediate 12 (1.45 g) and piperidient (5 ml) in butan-1-ol (10 ml), except that F.C.C. (B) was carried out with EA:methanol (19:1) and then EA:methanol:-triethylamine (94:5:1) as eluent.

INTERMEDIATE 19

[1α,(Z),2β,5β]-(±)-1,1'-Dimethylethyl 6-[[2-[(4-bromophenyl)methoxy]-5-(hexahydro-1H-azepin-1-yl)cyclopentyl]oxy]-4-hexenoate Sodium hydride (80%, 0.11 g) was added under nitrogen to a solution of Intermediate 13 (0.85 g) in dry DMF (8.5 ml). The mixture was heated at 70° until evolution of hydrogen had ceased. The suspension was cooled (0°) and Intermediate 5 (0.76 g) was added dropwise. The mixture was stirred at 20° for 4.5 h poured into brine and extracted with ER. the organic extracts were dried, filtered and evaporated to give an orange oil. F.C.C. (B) with ER as eluent gave the title compound as a yellow-brown oil (0.52 g).

Analysis Found: C,62.5; H,7.9; N,2.65.
$C_{28}H_{42}BrNO_4$ requires C,62.7; H,7.9; N,2.6%.

In a similar manner were prepared Intermediates 20–24.

INTERMEDIATE 20

[1α(Z),2α,5β]-(±)-1,1'-Dimethylethyl 6-[[2-[(4-bromophenyl)methoxy]-5-(hexahydrol-1H-azepin-1-yl)cyclopentyl]oxy]-4-hexenoate (5.90 g)

Analysis Found: C,62.8; H,8.0; N,2.8.
$C_{28}H_{42}BrNO_4$ requires C,62.7; H,7.9; N,2.6%.

From sodium hydride (801%, 2.63 g), Intermediate 5 (8.5 g) and Intermediate 14 (13.7 g) in dry DMF (40 ml) except that F.C.C. (B) was carried out with ER:hexane (1:1) as eluent.

INTERMEDIATE 21

[1α(Z),2β,5β]-(±)-1,1-Dimethylethyl 6-[[2-[(4-bromophenyl)methoxy]-5-(4-morpholinyl)cyclopentyl]oxy]-4-hexenoate (10.66 g)

T.l.c. (B) ER Rf 0.34.
Analysis found: C,59.5;H,7.5;N,2.8.
$C_{26}H_{38}BrNO_5$ requires C,59.5;H,7.3;N,2.7%.

From sodium hydride (80%, 1.78 g), Intermediate 5 (11 g) and Intermediate 15 (12.58 g) in dry DMF (80 ml) except that Intermediate 5 was added rapidly and then the mixture was stirred at 0° for 10 min, then the cooling bath was removed, and stirring was continued for 2.5 h. Water (20 ml) was added dropwise, and the resulting mixture was poured onto more water l(500 ml) and extracted with EA (3×150 ml). The combined organic extracts were washed with water (500 ml) and brine (250 ml), and then dried, and evaporated in vacuo to leave a brown oil. Finally, the oil was purified by F.C.C. eluting with ER:hexane (1:2) then (2:1) then ER.

INTERMEDIATE 22

[1α(Z),2β,5β]-(±)-1,1-Dimethylethyl-6-[[2-[(4-bromophenyl)methoxy]-5-(1-piperidinyl)cyclopentyl]oxy]-4-hexenoate (5.2 g)

T.l.c. (B) ER 0.67.

From sodium hydride (80%, 1.57 g), Intermediate 5 (10 g) and Intermediate 16 (10.86 g) in dry DMF (70 ml) except that the work-up procedure was as described in Intermediate 21 above using F.C.C. (B) eluting with hexane:ER (3:1), then (2:1) and finally (1:1).

INTERMEDIATE 23

[1α(Z),2β,5β]-(±)-1,1-Dimethylethyl 6-[[2-[3-(4-bromophenyl)propoxy]-5-(1-piperidinyl)cyclopentyl]oxy]-4-hexenoate (1.17 g)

T.l.c. (B) hexane:EA (2:1) Rf 0.25.

From sodium hydride (380 mg, 80%), Intermediate 5 (1.6 g) and Intermediate 18 (1.53 g) in dry DMF (7.0 ml) except that the work-up procedure was as described in Intermediate 21 above using F.C.C. (B) eluting with hexane:EA (9:1), (5:1) and finally (4:1).

INTERMEDIATE 24

[1α(Z),2β,5β]-(±)-1,1-Dimethylethyl 6-[[2-[(3-bromophenyl)methoxy]-5-(hexahydro-1H-azepin-1-yl)cyclopentyl]oxy]-4hexenoate (11.4 g)

T.l.c. (B) hexane:EA (2:1l) Rf 0.37.

From sodium hydride (801%, 4.3 g), Intermediate 5 (20 ml) and Intermediate 17 (16.8 g) in DMF (75 ml). except that the work-up procedure was as described in Intermediate 21 above using F.C.C. (B) eluting with hexane:EA (2:1).

INTERMEDIATE 25

[1α,(Z),2β,5β]-(±)-6-[[2-[(4l-Bromophenyl)methoxy]-5-(hexahydro-1H-azepin-1-yl)cyclopentyl]oxy]-4-hexenoic acid A solution of Intermediate 19 (0.40 g) in ethanol (9 ml) was stirred with 2M sodium hydroxide solution (4 ml) and the resulting mixture heated under reflux for 2.5 h. The mixture was poured into pH 6.5 phosphate buffer (50 ml) and extracted with DCM. The organic extracts were dried, filtered and evaporated to give a pale yellow oil which was purified by F.C.C. (B) using triethylamine:methanol:EA (2:15:83) as eluent gave the title compound as a yellow oil (260 mg). T.l.c. (A) NH3:ethanol:DCM (4:25:71) Rf 0.43.

In a similar manner were prepared Intermediates 26–30.

INTERMEDIATE 26

[1α(Z),2α,5β]-6-[[2-(4-Bromophenyl)methoxy]-5-(hexahydro-1H-azepin-1-yl)cyclopentyl]oxyl]-4-hexenoic acid (5.09 g)

T.l.c. (A) DCM:ethanol:NH3 (75:20:5) Rf 0.33.

From Intermediate 20 (5.85 g) and 2N sodium hydroxide (25 ml) in ethanol (5 ml) except that the purification step was not required.

INTERMEDIATE 27

[1α(Z),2β,5β]-(±)-6-[[2-[(4-Bromophenyl)methoxy]-5(4-morpholinyl) cyclopentyl]oxy]-4-hexenoic acid (9.29 g), m.p. 99°–100°

T.l.c. (A) DCM:ethanol:NH$_3$ (14:5:1) Rf 0.24.

From Intermediate 21 (10.59 g) and sodium hydroxide (2M, 50 ml) in ethanol (100 ml) except that work-up was carried out by evaporating the mixture in vacuo and then pouring the mixture onto a mixture of pH 6.5 phosphate buffer (100 ml) and hydrochloric acid (2M; 50 ml), followed by extraction with DCM (3×50 ml). The combined organic extracts were dried and evaporated in vacuo to leave a brown oil which was purified by F.C.C. (A) eluting with DCM:ethanol:NH$_3$ (72:25:3).

INTERMEDIATE 28

[1αL(Z),2β,5β]-(±)-6-[[2-[(4-Bromophenyl)methoxy-5-(1-piperidinyl) -cyclopentyl]oxy]-4-hexenoic acid (6.53 g)

T.l.c. (A) DCM:ethanol:NH$_3$ (14:5:1) Rf 0.35

From Intermediate 22 (7.53 g) and sodium hydroxide (2M, 40 ml) in ethanol (80 ml) except that the work-up procedure was as described in Intermediate 27 above although the chromatography step was not required.

INTERMEDIATE 29

[1α(Z),2β,5β]-(±)-6l-[[2-[3-(4-Bromophenyl)propoxy]-5-(1-piperidinyl)-cyclopentyl]oxy]-4-hexenoic acid (1.03 g)

T.l.c. (A) DCM:ethanol:NH$_3$ (75:25:3.5) Rf 0.29.

From Intermediate 23 (1.15 g) and sodium hydroxide (2M, 6 ml) in ethanol (12 ml) except that work-up was carried out by treating the mixture with hydrochloric acid (2M, 6 ml), followed by pH 6.5 phosphate buffer (150 ml). the combined organic extracts were dried and evaporated.

INTERMEDIATE 30

[1α(Z),2β,5β]-(±)-6-[[2-[(3-Bromophenyl)methoxy]-5-(hexahydro-1H-azepin-1-yl)cyclopentyl]oxy]-4-hexenoic acid (10.0 g)

T.l.c. (A) DCM:ethanol:NH$_3$ (80:20:2) Rf 0.35

From Intermediate 24 (11.4 g) and sodium hydroxide (2M, 50 ml) in ethanol (100 ml) except that work-up was carried out by evaporating the mixture in vacuo and the aqueous residue was treated with hydrochloric acid (2M, 50 ml) and pH 6.5 phosphate buffer (500 ml) and then extracted with EA (4×150 ml), washed with brine (200 ml), dried and evaporated.

INTERMEDIATE 31

[1α(Z),2β,5β]-(±)-6-[[2-[(4-Boronophenyl)methoxy]-5-(hexahydro-1H-azepin-1-yl)cyclopentyl]oxy]-4-hexenoic acid, bimolecular monoanhydride n-Butyl lithium (1.6M; 3 ml) was added, over 10 min, under nitrogen, to a cooled (−78°) solution of Intermediate 25 (0.475 g) in dry THF (30 ml). After a further 12 min, triisopropyl borate (5 ml) was added over 30 sec. After a further 20 min, the cooling bath was removed and the mixture stirred for 2.5 h. Water (5 ml) was added and the solvent removed in vacuo to give a residue which was purified by F.C.C. (A), eluting with DCM:ethanol:NH$_3$ (90:60:12) to give a solid which was evaporated with water (1 ml) to give the title compound as a solid (0.122 g).

Analysis Found: C,65.95; H,8.3; N,3.5. $C_{48}H_{70}B_2N_2O_{11}$ requires C,66.1; H,8.1; N,3.2%.

INTERMEDIATE 32

[1α(Z),2α,5β]-(±)-6-[[2-[(4-Boronophenyl)methoxy]-5-(hexahydro-1H-azepin-1yl)cyclopentyl]oxy]-4-hexenoic acid n-Butyllithium (1.3M; 30 ml) was added dropwise over 20 min (keeping internal temperature <−95°) under nitrogen to a stirred solution of Intermediate 26 (2 g) and triisopropylborate (19 ml) in dry THF (100 ml). After stirring at −100° for 10 min, the mixture was allowed to warm to room temperature over 3h. Methanol (50 ml) and then water (15 ml) were added dropwise. The mixture was evaporated in vacuo to leave a grey solid. F.C.C. (A) eluting with DCM:ethanol:NH$_3$ (70:20:5) then DCM:ethanol:methanol:NH$_3$ (5:2:2:1) gave the title compound as a cream foam.

T.l.c. (A) DCM:ethanol:methanol:NH$_3$ (5:2:2:1) Rf 0.41.

INTERMEDIATE 33

[4-[[(1,1-Dimethylethyl)dimethylsilyl]oxy]phenyl]boronic acid, bimolecular monoanhydride n-Butyl lithium (1.6M; 9.7 ml) was added, over 8 min. under nitrogen, to a stirred, cooled (<−70°) solution of 1-bromo-4-[[(1,1-dimethylethyl)dimethylsilyl]oxy]benzene (4 g) in dry THF (40 ml). After a further 25 min, the resulting solution was added over 10 min. (keeping internal temp. <−66°) to a stirred cooled solution or tri-isopropyl borate (10 ml) in THF (40 ml). The cooling bath was then removed and the mixture stirred for 2 h. Water (10 ml) and, after a further 5 min, pH 6.5 phosphate buffer (100 ml) and ether (50 ml) were added and the mixture stirred vigorously for 10 min. The aqueous layer was extracted with ER (2×70 ml) and the combined organic solutions dried and evaporated in vacuo to leave a white solid. Crystallization from ER gave the title compound (2.02 g) as a white solid, m.p. 193°–7°.

INTERMEDIATE 34

[1R-[1α,2β,5β]]-2-[(4Bromophenyl)methoxy]-5-(hexahydro-1H-azepin-1-yl)cyclopentan-1-ol (D)-dibenzoyl tartaric acid salt and

[1S-[1α,2β,5β]]-2-[(4-bromophenyl)methoxy]-5-(hexahydro-1H-azepin-1-yl)cyclopentan-1-ol (L)-dibenzoyl tartaric acid salt A mixture of Intermediate 13 (15 g) and (L)-dibenzoyl tartaric acid (15.33 g) was heated in ethyl acetate (200 ml) with addition of methanol until dissolved. The mixture was allowed to cool whereupon a white solid crystallized which was collected by filtration. This solid was recrystallized from 10% methanol in ethyl acetate (with addition of methanol until totally dissolved). On standing in a fridge for 36 h barge clumps of off-white crystals formed, which were collected and dried under vacuum to give the title (1S) salt (9.6 g), m.p. 158° dec.

The mother liquors from the above reaction were basified (2N sodium hydroxide solution) and extracted into ether, dried (MgSO$_4$) and concentrated. The concentrate and (D)-dibenzoyltartaric acid (11.45 g) were dissolved in an ethyl acetate:methanol (10:1) mixture at reflux, with addition of methanol to complete dissolution. On cooling in a fridge (56 h) off-white crystals formed. These were collected by filtration and dried under vacuum to give the title (1R) salt (10.02 g) m.p. 155° dec.

INTERMEDIATE 35

[1R-[1α,2β,5β]]-2-[(4-Bromophenyl)methoxy]-5-(hexahydro-1H-azepin-1-yl)cyclopentan-1-ol Sodium hydroxide (2N; 75 ml) was added to the (1R) salt of Intermediate 34 (4.04 g) and the mixture stirred until the salt had dissolved. The phases were separated and the aqueous extracted with dichloromethane (50 ml), combined organic phases dried (MgSO$_4$) and evaporated to give the title compound as a colorless oil (2.08 g). T.l.c. SiO$_2$ [ether:hexane (3:1);Et$_3$N doped] Rf 0.04. $[\alpha]_D^{20}$= +1.72° (ethanol).

INTERMEDIATE 36

[1S-[1α,2β,5β]]-2-[(4l-Bromophenyl)methoxy]-5-hexahydro-1H-azepin-1-yl) cyclopentan-1-ol Sodium hydroxide (2N:75 ml) was added to the (1S) salt of Intermediate 34 (4.04 g) in dichloromethane (50 ml) and the mixture stirred until the salt had dissolved. The phases were separated and the aqueous extracted with dichloromethane (50 ml). combined organic phases were dried (MgSO$_4$) and evaporated to give the title compound (2.11 g) as a colorless oil. T.l.c. SiO$_2$ [ether:hexane (3:1);Et$_3$N doped] Rf 0.04 ·$[\alpha_D^{20}$= -1.64° (ethanol).

INTERMEDIATE 37

[1R-[1α(Z),2β,5β]]-1,1'-Dimethylethyl 6-[[2-[(4-bromophenyl)methoxy]-5-(hexahydro-1H-azepin-1-yl)cyclopentyl]oxy]-4l-hexenoate To a solution of Intermediate 35 (2.02 g) in dry dimethylformamide under nitrogen was added sodium hydride (80l% in oil, 263 mg). The mixture was warmed until vigorous hydrogen evolution occurred. When effervescence had ceased the suspension was cooled to 0° and (Z)-1,1-dimethylethyl 6-chloro-4-hexenoate (1.8 ml) was added. The mixture was stirred for 2 h, diluted with water (1200 ml) and extracted with ether (3×50 ml). Combined extracts were washed with water, dried (MgSO$_4$) and evaporated to give a solid. Purification by chromatography [Fluka HF$_{254}$ SiO$_2$ pretreated with triethylamine] eluting with ether:hexane (3:1)→ethyl acetate:ethanol (1:1l) gave the title compound (1.28 g) as a light yellow oil. T.l.c. SiO$_2$ [ether:hexane (3:1); Et$_3$N doped] Rf 0.35·$[\alpha]_C^{20}$= -0.37° (ethanol).

INTERMEDIATE 38

[1S-[1α(Z),2β,5β]]-1,1'-Dimethylethyl 6-[[2l-[(4-bromophenyl)methoxy]-5-(hexahydro-1H-azepin-1yl)cyclopentyl]oxy]-4-hexenoate To a solution of Intermediate 36 (2.05 g) in dry dimethylformamide (20 ml) was added sodium hydride (80% in oil, 270 mg). The mixture under nitrogen was heated to 60° until hydrogen evolution ceased. (Z)-1,1-dimethylethyl 6-chloro-4-hexenoate (1.82 ml) was added dropwise to the solution at 0° and stirred for 2 h. Water (50 ml) and brine (50 ml) were added and extracted with ethyl acetate (3×50 ml). combined extracts were washed with water, dried (MgSO$_4$) and evaporated to a solid. Purification by chromatography [Fluka HF$_{254}$ SiO$_2$ pretreated with triethylamine] eluting with ether:hexane (3:1)→ether:ethanol (4:1) gave the title compound (780 mg) as a colorless oil. T.l.c. SiO$_2$ [ether:hexane (3:1); Et$_3$N doped] Rf 0.35. $[\alpha]_D^{20}$= +0.52° (ethanol).

INTERMEDIATE 39

[1R-1α(Z),2β,5β]]-6-[[2l-[(4-Bromophenyl)methoxy]-5-(hexahydro-1H-azepin-1l-yl)cyclopentyl]oxy]-4-hexenoic acid To a solution of Intermediate 37 (1.24 g) in ethanol (15 ml) was added sodium hydroxide solution (2N;5 ml). The solution was allowed to stand at room temperature for 24 h, heated at reflux for 2 h, neutralized with 2N hydrochloric acid and diluted with pH 6.5 buffer (50 ml). the aqueous mixture was extracted with dichloromethane (3×50 ml). Combined extracts were dried (MgSO$_4$) and evaporated to give the title compound (1.16 g) as a colorless gum. T.l.c. SiO$_2$ [ethyl acetate:ethanol (2:1), 1% NH$_3$]Rf 0.1. $[\alpha]_D^{20}$= +38.98° (chloroform).

INTERMEDIATE 40

[1S-[1α(Z),2β,5β]]-6-[[2-[(4-Bromophenyl)methoxy]-5-(hexahydro-1H-azepin-1-yl)cyclopentyl]oxy]-4-hexenoic acid To a solution of Intermediate 38 (743 mg) in ethanol (10 ml) was added sodium hydroxide solution (2N;3 ml) and the mixture allowed to stand at room temperature for 24 h, then heated at reflux for 2 h. The mixture was neutralized (2N HCl), diluted with pH 6.5 buffer (50 ml) and extracted with dichloromethane (3×50 ml). combined extracts were dried (MgSO$_4$) to give the title compound (392 mg) as a colorless gum. T.l.c. SiO$_2$ [ethyl acetate:ethanol (2:1), 1% NH$_3$] Rf 0.1. $[\alpha]_D^{20}$= -37.18° (chloroform).

EXAMPLE 1(a)

[1α(Z),2β,5β]-6-[[2-(Hexahydro-1H-azepin-1-yl)-5-[[2'-(hydroxymethyl)[1,1'-biphenyl]-4-yl]methoxy]cyclopentyl]oxy]-4-hexenoic acid A mixture of the Intermediate 25 (0.195 g), 1,3-dihydro-1-hydroxy-2,1-benzoxaborole (0.135 g), TTP (0.018 g), aqueous 1M sodium carbonate (2.5 ml) and 1,2-dimethoxyethane (6.5 ml) was stirred and heated at reflux under nitrogen for 3 h. 2N Sulfuric acid (1.5 ml) and pH 6.5 phosphate buffer (40 ml) were added to the cooled mixture which was extracted with DCM. The organic extracts were dried and evaporated. F.C.C. (A) eluting with DCM:ethanol:NH$_3$ (86:16:2) gave a cream colored foam which was dissolved in 0.5N sulfuric acid and washed with ER. The aqueous layer was neutralized with 5N sodium hydroxide, pH6.5 phosphate buffer added and the product was extracted into DCM. Evaporation of the dried organic extract gave the title compound (0.195 g) as a pale cream foam. I.r. (CHBr$_3$) 760, 830, 1600(br), 1700(br), 3595cm$^{-1}$.

T.l.c. (A) (82:16:2) DCM:ethanol:NH$_3$ Rf 0.19.

The following compounds were prepared by the same method from a suitable bromo intermediate and a boron reagent:

(b)

[1α(Z),2β,5β]-(±)-6-[[2-(Hexahydro-1H-azepin-1-yl)-5-[[4'-(hydroxymethyl) [1,1'-biphenyl]-4-yl]methoxy]cyclopentyl]oxy]-4-hexenoic acid T.l.c. (A) DCM:ethanol:NH$_3$ (39:10:1) Rf 0.24.

Anaylsis Found: C,73.2: H,8.2; N,2.5.
C31H41NO5 requires C,73.3; H,8.1; N,2.8%

(c)

[1α(Z),2β,5β]-(±)-6-[[2-(Hexahydrol-1H-azepin-1-yl)-5-[[3'-hydroxymethyl)[1,1'-biphenyl]-4-yl]methoxy]cyclopentyl]oxy]-4-hexenoic acid I.r. (CHBr3) 788, 830, 1600, 1705(br) cm⁻¹. T.l.c. (A) DCM:ethanol:NH3 (67:30:3) Rf 0.18.

(d)

[1α(Z),2β,5β]-(±)-6-[[2-(Hexahydrol-1H-azepin-1-yl)-5l-[(4'-hydroxy[1,1'-biphenyl]-4-yl)methoxy]cyclopentyl]oxy]-4-hexenoic acid.

I.r. (Nujol) 815, 1560, 1712 (br), 3700 (br) cm⁻¹. T.l.c. (A) DCM:ethanol:NH3 (82:16:2) Rf 0.17.

(e)

[1α,2β(Z),3α]-(±)-4'-[[[2-[(5-Carboxy-2-penten-1-yl)oxy]-3-(hexahydro-1H-azepin-1-yl)cyclopentyl]oxy]-methyl]-1,1'-biphenyl-3-carboxylic acid I.r. (Nujol) 768, 1562, 1710, 3700 (br) cm⁻¹. T.l.c. (A) DCM:ethanol:methanol:NH3 (25:12:12:1) Rf 0.15.

(f)

[1α(Z),2β,5β]-(±)-6-[[2-(Hexahydrol-1H-azepin-1-yl)-5-[(2'-hydroxy
[1,1-biphenyl]-4-yl)methoxy]cyclopentyl]oxy]-4-hexenoic acid M.P. 149°-151°.

Analysis Found: C,72.7; H,7.9; N,2.6.
C30H39NO5 requires C,73.0; H,8.0; N,2.8%.

(g)

[1α(Z),2β,5β]-(±)-6-[[2-[[4'-(Aminocarbonyl)]1,1'-biphenyl]-4-yl]-methoxy]-5-(hexahydro-1H-azepin-1-yl)cyclopentyl]oxy]-4-hexenoic acid I.r. (Nujol) 820, 1610, 1665, 1710 (sh) cm⁻¹. T.l.c. (A) DCM:ethanol:NH3 (67:30:3) Rf 0.15.

(h)

[1α(Z),2β,5α]-(±)-6-[[2-(Hexahydro-1H-azepin-1-yl)-5-[[4'-(hydroxymethyl)
[1,1'-biphenyl]4-yl]methoxy]cyclopentyl]oxy]-4-hexenoic acid T.l.c. (A) DCM:ethanol:NH3 (55:40:5) Rf 0.22. I.r. (CHBr3) 805, 1600(br), 1700, 3590 cm⁻¹.

(i)

[1α(Z'),2β,5α]-6-(±)-[[2-(Hexahydro-1H-azepin-1-yl)-5-[[3'-(hydroxymethyl)
[1,1'-biphenyl]-4-yl]methoxy]cyclopentyl]oxy]-4-hexenoic acid I.r. (Nujol) 785, 830, 1710 (br), 3450 (br) cm⁻¹. T.l.c. (A) DCM:ethanol:NH3 (70:25:5) Rf 0.15.

(j)

[1α(Z),2β,5α]-(±)-6-[[2-(Hexahydro-1H-azepin-1-yl)-5-[[2'-(hydroxymethyl)
[1,1'-biphenyl]-4-yl]methoxy]cyclopentyl]oxy]-4-hexenoic acid T.l.c. (A) DCM:ethanol:NH3 (13:6:1) Rf 0.35. I.r. (CHBr3) 765, 1595, 1710, 3595 cm⁻¹.

(k)

[1α(Z),2β,5β]-(±)-6-[[2-[[2'-(Hydroxymethyl)[1,1'-biphenyl]-4-yl]methoxy]-5-(4-morpholinyl)cyclopentyl]oxy]-4-hexenoic acid.

T.l.c. (A) DCM:ethanol:NH3 (14:5:1) Rf 0.27.
Analysis Found: C,68.3; H,8.0; N,2.9.
C29H37NO6 requires C,780.3; H,7.5; H,2.8%.
C29H37NO6 (0.9 molH2OL)Cf,68.1; H,7.6; N,2.7%.

(l)

[1α(Z),2β,5β]-(±)-6-[[2-[[2'-(Hydroxymethyl)[1,1'-biphenyl]-4yl-methoxy]-5-(1-piperidinyl)cyclopentyl]oxy]-4-hexenoic acid T.l.c. (A) DCM:ethanol:NH3 (14:5:1) Rf 0:25.
Analysis Found: C,72.7; H,8.1; N,2.7.
C30H39NO5 requires C,73.0; H,8.0; N,2.8%.

(m) [1α(Z),
2β,5β]-(±)-6-[[2-[3-[2'-(Hydroxymethyl)[1,1'-biphenyl]-4-yl]propoxy]-5-(1-piperidinyl)cyclopentyl]oxy]-4-hexenoic acid T.l.c. (A) ethanol:DCM:NH3 l(25:75:3) Rf 0.24. I.r. (CHBr3) 1730-1570 (br), 1065, 765 cm⁻¹.

(n)

[1α(Z),2β,5β]-(±)-6-[[2-Hexahydro-1H-azepin-1-yl)-5-[[2'-(hydroxymethyl)
[1,1'-biphenyl]-3-yl]methoxy]cyclopentyl]oxy]-4-hexenoic acid T.l.c. (A) DCM:ethanol:NH3 (25:8:1) Rf 0.26.
The gum l(271 mg) was dissolved in DCM (15 ml) and washed with pH 6.5 phosphate buffer (20 ml), then dried and evaporated to leave the title compound as a pale yellow foam (254 mg).
Analysis Found: C,72.2; H,8.2; N,2.6.
C31H41NO5 requires C,73.3; H,8.1; N,2.7%.

(o)

[1α(Z),2β,5β]-(±)-6-[[2-(Hexahydrol-1H-azepin-1-yl)-5-[[2'-(methylsulphonyl)
methyl][1,1'-biphenyl]-4-yl]methoxy]cyclopentyl]oxy]-4-hexenoic acid T.l.c. (A) DCM:ethanol:NH3 (75:25:3.5) Rf 0.43.
Analysis Found: C,6.3; H,7.75; N,2.2.
C32H43NO6S.O.58 H2O requires C,66.25; H,7.6; N,2.4%.

The following Table I is a summary of the reaction conditions used to prepare the products of Examples 1(b) to 1(o).

TABLE I

| Ex. No. | Intermediate used (and weight) | Boron reagent used (and weight) | Vol. of solvent (ml) | Vol. and concentration of Na2CO3 | Wt. of TTP (g) | Reaction Time (h) | Work-up procedure | Yield (g) |
|---------|-------------------------------|--------------------------------|----------------------|---------------------------------|----------------|-------------------|-------------------|-----------|
| 1b | (0.2 g) | a (0.18 g) | 5 | 2 ml, 2 N | 0.015 | 4.5 | A | 0.193 |
| 1c | (0.175 g) | b (0.08 g) | 5 | 2 ml, 2 N | 0.013 | 5 | B | 0.167 |
| 1d | (0.21 g) | c (0.225 g) | 6 | 2.5 ml, 2 N | 0.022 | 5 | C | 0.18 |
| 1e | (0.207 g) | d (0.14 g) | 8 | 3 ml, 2 N | 0.022 | 6 | D | 0.12 |
| 1f | (0.33 g) | e (0.22 g) | 10 | 5 ml, 2 N | 0.027 | 3 | E | 0.12 |
| 1g | (0.215 g) | f (0.12 g) | 8 | 3 ml, 2 N | 0.021 | 4 | F | 0.162 |

TABLE I-continued

| Ex. No. | Intermediate used (and weight) | Boron reagent used (and weight) | Vol. of solvent (ml) | Vol. and concentration of Na$_2$CO$_3$ | Wt. of TTP (g) | Reaction Time (h) | Work-up procedure | Yield (g) |
| --- | --- | --- | --- | --- | --- | --- | --- | --- |
| 1h | (0.46 g) | a (0.317 g) | 10 | 5 ml, 2 N | 0.035 | 3.5 | G | 0.477 |
| 1i | (0.458 g) | b (0.319 g) | 10 | 5 ml, 2 N | 0.030 | 3 | H | 0.108 |
| 1j | (0.284 g) | g (0.2 g) | 10 | 5 ml, 2 N | 0.026 | 3.5 | I | 0.10 |
| 1k | (0.219 g) | g (0.2 g) | 10 | 5 ml, 2 N | 0.029 | 4.5 | J | 0.289 |
| 1l | (0.266 g) | g (0.166 g) | 10 | 5 ml, 2 N | 0.026 | 3.5 | J | 0.188 |
| 1m | (0.17 g) | g (0.065 g) | 3 | 1.5 ml, 1 M | 0.020 | 3 | K | 0.13 |
| 1n | (0.34 g) | g (0.156 g) | 5.5 | 2.75 ml, 1 M | 0.025 | 3 | L | 0.30 |
| 1o | (0.172 g) | h (0.114 g) | 3 | 1.5 ml, 1 M | 0.035 | 4.5 | M | 0.163 |

In column 3 of Table I above the boron reagents designated a-h are as follows:

a. [4-(hydroxymethyl)phenyl]boronic acid
b. [3-(hydroxymethyl)phenyl]boronic acid
c. [4-[[(1,1-dimethylethyl)dimethylsilyl]oxy]phenyl]boronic acid, bimolecular monoanhydride
d. 3-boronobenzoic acid
e. (2-hydroxyphenyl)boronic acid
f. [4-(aminocarbonyl)phenyl]boronic acid
g. 1,3-dihydro-1-hydroxy-2,1-benzoxaborole
h. [2-[(methylsulphonyl)methyl]phenyl]boronic acid.

In column 8 of Table I above the work-up procedures designated A-M are as follows:

A. 2N sulfuric acid (1 ml) was added to the cooled solution, which was then diluted with pH 6.5 phosphate buffer (50 ml) and extracted with DCM (4×20 ml). Evaporation of the dried extract gave a yellow gum which was subjected to F.C.C. (A) eluting with DCM:ethanol:NH$_3$ 1(78:20:2).

B. As in A above except that the eluting system was initially DCM:ethanol:NH$_3$ (78:20:2) and then DCM:ethanol:NH$_3$ (67:30:3).

C. As in A above except that extraction was carried out with EA instead of DCM and the eluting system was as in B above.

D. The mixture was diluted with 0.5N sodium carbonate (35 ml) and washed with ER (50 ml). The aqueous layer was acidified (pH<1) with concentrated hydrochloric acid and extracted with DCM (6×25 ml). Evaporation of the dried extract gave a yellow gum which was subjected to F.C.C. (A) eluting with DCM:ethanol:NH$_3$ (67:30:3) then DCM:ethanol:methanol:NH$_3$ (47:25:25:3).

E. The mixture was poured onto phosphate buffer (pH 6.5; 75 ml) containing 2N sulfuric acid (2.5 ml) and extracted with DCM (5×30 ml). the organic extracts were dried and evaporated in vacuo to leave a brown gum which was subjected to F.C.C. (A) eluting with DCM:ethanol:NH$_3$ (70:35:2) then (83:15:2).

F. 2N sulfuric acid (3 ml) was added to the mixture which was then diluted with phosphate buffer (pH 6.5; 70 ml) and extracted with DCM (4×30 ml). Evaporation of the dried extract gave a gum which was subjected to F.C.C. (A) eluting with DCM:ethanol:NH$_3$ (82:16:2) then (67:30:3).

G. As in A above except that 2.5 ml sulfuric acid and 100 ml phosphate buffer were used.

H. As in G above except that DCM:ethanol:NH$_3$ (78:20:2) was used as eluent.

I. Phosphate buffer (pH 6.5; 100 ml) was added to the mixture which was extracted with DCM, then dried and evaporated to leave a yellow oil which was purified by F.C.C. (A) eluting with DCM:ethanol:NH$_3$ (83:15:2).

J. As in E above except that DCM:ethanol:NH$_3$ (83:15:2) then (75:22:3) was used as eluent.

K. The mixture was poured into phosphate buffer (pH 6.5; 100 ml) and extracted with EA (4×10 ml). The combined extracts were dried and evaporated to give a yellow oil which was subjected to F.C.C. (A) eluting with ethanol:DCM:NH$_3$ (25:75:3).

L. The mixture was filtered and the filtrate treated with 2N hydrochloric acid (30 ml). The organic solvents were evaporated and the aqueous residue was washed with ER and extracted with DCM (3×20 ml). The DCM extracts were evaporated to ca. 20 ml, washed with phosphate buffer (pH 6.5, 3×50 ml) and evaporated. The residual foam was subjected to F.C.C. (A) eluting with DCM:ethanol:NH$_3$ (80:18:2) then (80:17:3).

M. The mixture was treated with 1N sulfuric acid (1.5 ml), poured into phosphate buffer (pH 6.5; 100 ml) and then extracted with DCM (4×20 ml). the combined organic extracts were dried and evaporated to give a yellow oil which was subjected to F.C.C. (A) eluting with DCM:ethanol:NH$_3$ (75:25:3.5).

EXAMPLE 2(a)

[1α(Z),2β,5β]-(±)-6-[[2-[[4'-(2-amino-2-oxoethyl)[1,1'-biphenyl]-4-yl]methoxy]-5-(hexahydro-1H-azepin-1-yl)cyclopentyl]oxy]-4-hexenoic acid A mixture of Intermediate 31 (0.19 g), 4-bromophenyl acetamide (0.297 g), TTP (0.022 g), aqueous 2N sodium carbonate (2.5 ml) and 1,2-dimethoxyethane (7 ml) was stirred and refluxed under nitrogen for 5 h. 2N Sulfuric acid (2 ml) was added, then the mixture diluted with pH 6.5 phosphate buffer (50 ml) and extracted with DCM. Evaporation of the dried organic extract gave a yellow solid, which was purified by F.C.C. (A) eluting with DCM:ethanol:NH$_3$ (82:16:2) to give the title compound (0.185 g) as a yellow foam. T.l.c. (A) DCM:ethanol:NH$_3$ (67:30:3) Rf 0.10. I.r. (CHBr$_3$) 800, 1590, 1678, 1750, 351 cm$^{-1}$.

The following compounds were prepared by the same method from a suitable boronic acid derivative and a substituted halobenzene:

(b)

[1α(Z),2β,5β]-(±)-6-[[2-(Hexahydro-1H-azepin-1-yl)-5-[[4'-[[(methylamino)sulphonyl]methyl][1,1'-biphenyl]-4-yl]methoxy]cyclopentyl]oxy]-4-hexenoic acid T.l.c. (A) DCM:ethanol:NH$_3$ (67:30:3; run twice) Rf 0.53.

Analysis Found: C,64.3; H,7.5; N,4.5.
C$_{32}$H$_{44}$N$_2$O$_6$S requires C,65.7; H,7.6; N,4.8%.

(c)
[1α(Z),2β,5β]-(±)-6-[[2-[[4'-(Acetylamino)[1,1'-biphenyl]-4-yl]methoxy]-5-(hexahydro-1H-azepin-1-yl)cyclopentyl]oxy]-4-hexenoic acid T.l.c. (A) DCM:ethanol:NH$_3$ (68:30:2; run twice) Rf 0.45.
Analysis Found: C,71.7; H,8.5; N,4.7.
C$_{33}$H$_{44}$N$_2$O$_5$ requires C,72.2; H,8.1; N,5.1%.

(d)
[1α(Z),2β,5β]-(±)-6-[[2-(Hexahydro-1H-azepin-1yl)-5-[[3'-[(methylsulphonyl)amino][1,1'-biphenyl]-4-yl]methoxy]cyclopentyl]oxy]-4-hexenoic acid T.l.c. (A) DCM:ethanol:NH$_3$ (14:5:1) Rf 0.27
Analysis Found: C,63.4; H,7.6; N,4.7.
C$_{31}$H$_{42}$N$_2$O$_6$S requires C,65.2, H,7.4; N,4.9%.
[C$_{31}$H$_{42}$N$_2$O$_6$S.H$_2$O requires C,63.3; H,7.5; N,4.8%].

(e)
[1α(Z),2β,5α]-(±)-6-[[2-(Hexahydro-1H-azepin-1-yl)-5-[[2'-[(methylsulphonyl)amino][1,1'-biphenyl]-4-yl]methoxy]cyclopentyl]oxy]-4-hexenoic acid T.l.c. (A) DCM:ethanol:NH$_3$ (14:5:1) Rf 0.30.
Analysis found: C,63.8; H,7.1; N,4.4.
C$_{31}$H$_{42}$N$_2$O$_6$S requires C,65.2; H,7.4; N,4.9.
C$_{31}$H$_{42}$N$_2$O$_6$S.H$_2$O requires C,63.3; H,7.5; N,4.8%.

(f)
[1α(Z),2β,5β]-(±)-6-[[[2-[2'-[(Aminocarbonyl)amino][1,1'-biphenyl]-4-yl]methoxy]-5-(hexahydro-1H-azepin-1-yl)cyclopentyl]oxy]-4-hexenoic acid T.l.c. (A) DCM:ethanol:NH$_3$ (13:6:1) Rf 0.39.
Analysis Found: C,67.3;H,7.7;N,7.2.
C$_{31}$H$_{41}$N$_3$O$_4$ requires C,69.5;H,7.7;N,7.8%.
C$_{31}$H$_{41}$N$_3$O$_5$.H$_2$O requires C,67.3;H,7.8;N,7.6%.

(g)
[1α(Z),2β,5β]-(±)-6-[[2-(Hexahydro-1H-azepin-1-yl)-5-[[2'-[(methylsulphonyl)amino][1,1'-biphenyl]-4-yl]methoxy]cyclopentyl]oxy]-4-hexenoic acid T.l.c. (A) DCM:ethanol:NH$_3$ (14:5:1) Rf 0.49.
Analysis Found: C,65.2; H,7.2; N,4.6.
C$_{31}$H$_{42}$N$_2$O$_6$S requires: C,65.2; H,7.4; N,4.9%.

(h)
[1α(Z),2β,5β]-(±)-6-[[2-[[[2'-[(Acetylamino)methyl]]-[1,1'-biphenyl]-4-yl]methoxy]-5-[hexahydro-1H-azepin-1-yl]cyclopentyl]oxy]-4-hexenoic acid T.l.c. (A) DCM:ethanol:NH$_3$ (14:5:1) Rf 0.46.
Analysis Found: C,69.3;H,8.1;N,4.8.
C$_{33}$H$_{44}$N$_2$O$_5$ requires C,72.2;H,8.1;N,5.1.
C$_{33}$H$_{44}$N$_2$O$_5$.1.2 mol H$_2$O requires C,69.5;H,8.1;N,4.9%.

(i)
[1α(Z),2β,5β]-(±)-6l-[[2-[[2'-[[1,1-Dimethylethoxy)carbonyl]methyl][1,1'-biphenyl]-4-yl]methoxy]-5-(hexahydro-1H-azepin-1-yl) cyclopentyl]oxy]-4-hexenoic acid T.l.c. (A) DCM:ethanol:NH$_3$ (14:5:1); Rf 0.71.
Analysis Found: C,70.7; H,8.5; N,2.1.
C$_{36}$H$_{49}$NO$_6$ requires C,73.1; H,8.3; N,2..
C$_{36}$H$_{49}$NO$_6$.H$_2$O requires C,70.9;H,8.0; N,2.3%.

(j)
[1α(Z),2β,5β]-(±)-6-[[2-(Hexahydrol-1H-azepin-11-yl)-5-[[2'-(hydroxyethyl)[1,1'-biphenyl]-4-yl]methoxy]cyclopentyl]oxy]-4-hexenoic acid T.l.c. (A) DCM:ethanol:NH$_3$ (25:8:1) Rf 0.25.
Analysis Found: C,71.5; H,8.0; N,2.51.
C$_{32}$H$_{43}$NO$_5$ requires C,73.67; H,8.31; N,2.68.
C$_{32}$H$_{43}$NO$_5$.H$_2$O requires C,71.15; H,8.34; N,2.59%.

(k)
[1α(Z),2β,5β]-(±)-6-[[2-[[2'-(2-Amino-2-oxoethyl)[1,1'-biphenyl]-4yl]methoxy]-5-(hexahydro-1H-azepin-1-yl)cyclopentyl]oxy]-4-hexenoic acid hydrochloride I.r. (CHBr$_3$) 1600, 1675, 2200, 3400 cm$^{-1}$. T.l.c. (A) ER:methanol (3:1) Run twice Rf 0.2.

The title compound as a foam (0.45 g) was dissolved in DCM (0.1 ml) before adding ethereal hydrogen chloride to precipitate the title compound as an off-white solid (34 mg) which was washed with ER (2×5 ml) and dried in vacuo.

Analysis found: C,64.06; H,7.86; N,4.41.
C$_{32}$H$_{42}$N$_2$O$_5$.HCl requires C,67.29; H,7.59; N,4.9.
C$_{32}$H$_{42}$N$_2$O$_5$.HCl 1.5 H$_2$O requires C,64.19; H,7.68; N,4.68%.

(l)
[1α(Z),2β,5β]-(±)-6-[[2-[[2'-(Aminocarbonyl)[1,1'-biphenyl[-4-yl]methoxy]-5-(hexahydro-1H-azepin-1-yl)cyclopentyl]oxy]-4-hexenoic acid T.l.c. (A) DCM:ethanol:NH$_3$ (25:8:1) Rf 0.2.
Analysis Found: C,69.55; H,7.90; N,4.98.
C$_{31}$H$_{40}$N$_2$O$_5$.0.9 H$_2$O requires C,69.52; H,7.81; N,5.23%.

(m)
[1α(Z),2β,5β]-(±)-6-[[2-[[2'-[(dimethylamino)methyl]-[1,1'-biphenyl]-4-yl]methoxy]-5-(hexahydro-1H-azepin-1-yl)cyclopentyl]oxy]-4-hexenoic acid T.l.c. (A) DCM:ethanol:NH$_3$ (75:25:4) Rf 0.52.
Analysis Found: C,71.8; H,8.8; N,41.8.
C$_{33}$H$_{46}$N$_2$O$_4$ requires C,74.1; H,8.7; N,5.2.
C$_{33}$H$_{46}$N$_2$O$_4$.H$_2$O requires C,71.8; H,8.7; N,5.1%.

(n)
[1α(Z),2β,5β]-(±)-6-[[2-(Hexahydro-1H-azepin-1-yl)-5-[[2'-[[(methylamino)sulphonyl]methyl][1,1'-biphenyl]-4-yl]methoxy] cyclopentyl]oxy]-4-hexenoic acid T.l.c. (A) ER:methanol (run twice) Rf 0.28.
Analysis Found: C,63.0; H,7.3; N,4.4.
C$_{32}$H$_{44}$N$_2$O$_6$S requires C,65.7; H,7.6; N,4.8%.
C$_{32}$H$_{44}$N$_2$O$_6$S.H$_2$O requires C,63.8; H,7.7; N,4.65%.

(o) [1α,2β(Z),3α]-(±)-Methyl 4'-[[[[2-[(5-carboxy-2-penten-1-yl)oxy]-3l-(hexahydro-1H-azepin-1-yl)]cyclopentyl]oxy]methyl][1,1'-biphenyl]-2-carboxylate T.l.c. (A) DCM:ethanol:NH$_3$ (14:6:1) Rf 0.33.
The following Table II is a summary of the reaction conditions used to prepare the products of Examples 2(b) to 2(o).

TABLE II

| Ex. No. | Intermediate used (and weight) | Halobenzene used (and weight) | Vol. of solvent (ml) | Vol. and concentration of Na$_2$CO$_3$ | Wt. of TTP (g) | Reaction Time (h) | Work-up procedure | Yield (g) |
|---|---|---|---|---|---|---|---|---|
| 2b | (0.2 g) | a (0.2 g) | 6 | 2.5 ml, 2 N | 0.022 | 4 | A | 0.115 |
| 2c | (0.185 g) | b (0.16 g) | 6 | 2.5 ml, 2 N | 0.022 | 6 | B | 0.103 |
| 2d | (0.204 g) | c (0.22 g) | 10 | 5 ml, 2 N | 0.04 | 3 | C | 0.051 |
| 2e | (0.26 g) | d (0.229 g) | 10 | 6 ml, 2 N | 0.038 | 5 | A | 0.174 |
| 2f | (0.189 g) | e (0.113 g) | 10 | 5 ml, 2 N | 0.025 | 4 | E | 0.163 |
| 2g | (0.207 g) | d (0.248 g) | 10 | 5 ml, 1 M | 0.034 | 4 | F | 0.137 |
| 2h | (0.21 g) | f (0.228 g) | 10 | 6 ml, 2 N | 0.031 | 4 | G | 0.15 |
| 2i | (0.38 g) | g (0.45 g) | 20 | 10 ml, 1 M | 0.07 | 2.5 | H | 0.459 |
| 2j | (0.22 g) | h (0.34 g) | 7 | 2.5 ml, 1 M | 0.03 | 2.5 | I | 0.174 |
| 2k | (0.22 g) | i (0.235 g) | 7 | 2.5 ml, 1 M | 0.03 | 4 | J | 0.066 |
| 2l | (0.24 g) | j (0.215 g) | 8 | 3 ml, 1 M | 0.03 | 7 | K | 0.098 |
| 2m | (0.256 g) | k (0.13 g) | 5 | 2.5 ml, 1 M | 0.033 | 9 | L | 0.117 |
| 2n | (0.223 g) | l (0.2 g) | 10 | 3 ml, 2 N | 0.023 | 5.5 | M | 0.146 |
| 2o | (0.254 g) | m (0.188 g) | 5 | 2.5 ml; 1 M | 0.04 | 3 | N | 0.13 |

In column 3 of Table II above the halobenzene reagents designated a-m are as follows:

a. 4-iodo-N-methylbenzenemethanesulphonamide
b. [(4-bromophenyl)methyl]acetamide
c. N-(3-bromophenyl)methanesulphonamide
d. N-(2-bromophenyl)methanesulphonamide
e. (2-bromophenyl)urea
f. N-[(2-bromophenyl)methyl]acetamide
g. 1,1-dimethylethyl 2-bromobenzeneacetate
h. 2-bromobenzeneethanol
i. 2-bromophenylacetamide
j. 2-bromobenzamide
k. 2-bromo-N,N-dimethylbenzylamine
l. 2-bromo-N-methylbenzenemethanesulphonamide
m. 2-bromobenzoic acid In column 8 of Table II above the work-up procedures designated A-N are as follows:

A. 2N Sulfuric acid (3 ml) was added to the mixture which was then diluted with phosphate buffer (pH 6.5, 40 ml) and extracted with DCM (4×25 ml). Evaporation of the dried extract gave a yellow gum which was subjected to F.C.C. (A) eluting with DCM:ethanol:NH$_3$ (82:16:2) and rechromatographed (A) eluting with DCM:ethanol:NH$_3$ (85:13:1.5) then (82:16:2).

B. As in A above except that sulfuric acid 1(2.5 ml) and phosphate buffer (50 ml) were used and the initial chromatography used DCM:ethanol:NH$_3$ (82:16:2) then (75:23:2) as eluent.

C. Phosphate buffer (pH 6.5, 70 ml) and 2N sulfuric acid (2.5 ml) were added and the mixture was extracted with DCM (4×30 ml). The organic extracts were dried and evaporated in vacuo to give an oil which was subjected to F.C.C. (A) eluting with DCM:ethanol:NH$_3$ (75:20:5) and rechromatographed (A) eluting with DCM:ethanol:NH$_3$ (83:15:2).

D. The mixture was poured onto a mixture of phosphate buffer (pH 6.5, 50 ml) and 2N sulphuric acid (3 ml) and extracted with DCM (3×30 ml). The combined extracts were dried and evaporated in vacuo to leave an oil which was subjected to F.C.c. (A) eluting with DCM:ethanol:NH$_3$ (83:15:2) then (75:22:3).

E. As in D above except that DCM:ethanol:NH$_3$ (83:15:2) then (17:25:3) was used as eluent.

F. As in D above except that DCM:ethanol:NH$_3$ (83:15:2) was used as eluent.

G. As in D above except that the product was rechromatographed (A) eluting with DCM:ethanol:NH$_3$ (83:15:2).

H. As in F above except that the product of chromatography was dissolved in DCM (20 ml), washed with phosphate buffer (pH 6.5, 10 ml) and the aqueous layer extracted with DCM (20 ml). The combined organic extracts were dried and evaporated in vacuo.

I. 2N Sulphuric acid (2.5 ml) and phosphate buffer (pH 6.5, 30 ml) were added and the aqueous phase was extracted with DCM (3×40 ml). The organic extracts were evaporated to give an oil which was stirred at 35° with 5N hydrochloric acid (6 ml) and acetone (5 ml) for 0.5 h. The acetone was removed and the pH adjusted to 6 with solid potassium carbonate and phosphate buffer (pH 6.5, 40 ml) was then added. The aqueous mixture was extracted with DCM (3×50 ml) and the combined organic extracts were evaporated to leave an oil. This oil was chromatographed (A) at a pressure of 100 mm using DCM:ethanol:NH$_3$ (50:8:1) as eluent. The second fraction was evaporated.

J. 1M Sulphuric acid (3 ml) was added followed by phosphate buffer (pH 6.5, 40 ml). The mixture was extracted with DCM (4×40 ml) and the combined organic extracts were dried and elvaporated to leave a solid. The solid was subjected to chromatography (A) at a pressure of 100 mm using DCM:ethanol:NH$_3$ (50:8:1) as eluent. The second fraction was collected and purified by chromatography (A) at a pressure of 100 mm using ER:methanol (6:1→2:1) as eluent. The fourth fraction was collected and evaporated.

K. 1M Sulphuric acid (2.5 ml) and phosphate buffer (pH 6.5, 50 ml) were added. The mixture was extracted with DCM (3×50 ml) and the organic extracts were dried and evaporated to a gum which was purified by F.C.C. (A) at a pressure of 150 mm using DCM:ethanol:NH$_3$ (50:8:1) as eluent. The second fraction was collected and evaporated.

L. As in B above except that the initial chromatography used DCM:ethanol:NH$_3$ (75:25:2) then (75:25:4) and further purification by chromatography was not necessary.

M. 2N Sulfuric acid (3 ml) and phosphate buffer (pH 6.5, 100 ml) were added and the mixture extracted with DCM. The organic extract was dried and evaporated and the resulting gum was chromatographed (A) eluting with ER-methanol (3:1) then (2:1).

N. 2M Hydrochloric acid (2.5 ml) and phosphate buffer (pH 6.5, 75 ml) were added and the aqueous mixture extracted with EA (3×25 ml). The extract was acidified with 2M hydrochloric acid (20 ml) and extracted with DCM (3×25 ml). The combined organic extracts were dried and evaporated and the resulting oil was chromatographed (A) eluting with DCM:ethanol:NH$_3$ (15:6:0.5→15:6:1) to give a gum. The gum was dissolved in DCM, washed with phosphate buffer (pH 6.5) and dried.

EXAMPLE 3

[1α2β(A),3α]-(±)-4'-[[[2-[(5-Carboxy-2l-penten-1-yl)oxy]-3-(hexahydro-1H-azepin-1-yl)cyclopentyl]oxy]methyl][1,1'-biphenyl]-2-acetic acid A solution of the product of Example 2(i) (370 mg) in ethanol (6 ml) was stirred at reflux with sodium hydroxide (2M; 3 ml) under nitrogen for 4 h. The mixture was poured onto hydrochloric acid (2M; 25 ml) and extracted with DCM (3×25 ml). the combined organic extracts were dried and evaporated in vacuo to leave a grey gum. F.C.C. (A) eluting with DCM:ethanol:NH$_3$ (83:15:2) then DCM:ethanol (75:25) gave the title compound as a cream foam (105 mg). T.l.c. (A) DCM:ethanol:NH$_3$ (14:5:1) Rf 0.11. I.r. (CHBr$_3$) 3500–2300, 2500, 1710, 1600 cm$^{-1}$.

EXAMPLE 4

[1α,2β(Z),3α]-(±)-4'-[[[2-[(5-Carboxy-2-penten-1-yl)oxy]-3-(hexahydro-1H-azepin-1yl)cyclopentyl]oxy]methyl][1,1'-biphenyl]-2-carboxylic acid hydrochloride A solution of the product of Example 2(o) (130 mg) in ethanol (1.5 ml) was treated with sodium hydroxide (2M, 1.0 ml) and heated at reflux for 45 min. The mixture was poured into a mixture of pH 6.5 phosphate buffer (20 ml) and 2M hydrochloric acid (10 ml) and extracted with DCM (5×8 ml). The DCM extracts were dried and evaporated to give the title compound (126 mg) as a pale yellow gum. T.l.c. (A) DCM:ethanol:NH$_3$ (20:5:1) Rf 0.50. I.r. (CHBr$_3$) 3670, 3300–2200, 1700, 1600 cm$^{-1}$.

EXAMPLE 5

[1α,2β,5α]-(±)-6l-[[2-(Hexahydro-1H-azepin-1-yl)-5-[[2'-(hydroxymethyl)[1,1'-biphenyl]-4-yl]methoxy]cyclopentyl]oxy]hexanoic acid A solution of the product of Example 1(j) (0.2 g) in absolute ethanol (20 ml) was added under vacuum to wet 10% palladium on charcoal (120 mg). The vessels were flushed with hydrogen and the alkene was hydrogenated at 1 atmosphere and room temperature for 2 h. The mixture was filtered, washing with ethanol, and the filtrate was evaporated in vacuo to leave a brown gum. F.C.C. (A) eluting with DCM:ethanol:NH$_3$ (75:22:3) gave the title compound as a cream foam (126 mg). T.l.c. (A) DCM:ethanol:NH$_3$ (14:5:1) Rf 0.22.

Analysis Found: C,71.8;H,9.0;N,2.6.

C$_{31}$H$_{43}$NO$_5$ requires C,73.1;H,8.5;N,2.8%.
C$_{31}$H$_{43}$NO$_5$0.5 H$_2$O requires C,71.8;H,8.5;N,2.7%.

EXAMPLE 6

[1α,2β,5β]-(±)-6-[[2-(Hexahydro-1H-azepin-1-yl)-5-[[2'-(hydroxymethyl)[1,1'-biphenyl]-4-yl]methoxy]cyclopentyl]oxy]hexanoic acid A solution of the product of Example 1(a) (120 mg) in ethanol (10 ml) was added, under vacuum, to wet 10% palladium on carbon catalyst (40 mg) and the resulting slurry was hydrogenated at 1 atmosphere and room temperature with vigorous stirring. After 4 h the catalyst was filtered off and the filtrate was evaporated to leave an orange oil which was subjected to F.C.C. (A) eluting with DCM:ethanol:NH$_3$ (67:30:3) to give the title compound as a pale yellow oil (104 mg). T.l.c. (A) ethanol:DCM:NH$_3$ (20:80:3) (ran twice) Rf 0.08. I.r. (CHBr$_3$) 3600, 2700–1900 (br), 1700, 1600 cm$^{-1}$.

EXAMPLE 7

[1α(Z)2β,5β]-(±)-6-[[2-(Hexahydro-1H-azepin-1-yl)-5-[[2'-(hydroxymethyl)[1,1'-biphenyl]-4-yl]methoxy]cyclopentyl]oxy]-4-hexenoic acid, β-cyclodextrin complex (1:1)

A solution of the product of Example 1(a) (210 mg) in methanol (5 ml) was added to a solution of β-cyclodextrin (470 mg) in water (20 ml) and the solution was evaporated. The residue was dissolved in hot water (5 ml), filtered, and allowed to cool. The resulting suspension was filtered to give the title compound as a white solid (285 mg), m.p. >300° (darkens).

Analysis Found: C,49.5; H,6.6; N,0.8.

C$_{31}$H$_{41}$NO$_5$. C$_{42}$H$_{70}$O$_{35}$. 7 H$_2$O requires C,419.6; H,7.1; n,0.8%.

EXAMPLE 8

[1R-[1α(Z),2β,5β]]-6-[[2-(Hexahydro-1H-azepin-1-yl)-5-[[2'-(hydroxymethyl)[1,1'-biphenyl]-4-yl]methoxy]cyclopentyl]oxy]-4-hexenoic acid To a solution of Intermediate 39 (250 mg) in dimethoxyethane (8.5 ml) was added sodium carbonate solution (2N:3.5 ml), 1,3-dihydro-1-hydroxy-2,1-benzoxaborole (170 mg) and tetrakistriphenylphosphine palladium (OL) (23 mg). The mixture was heated at reflux under nitrogen for 3 h. After cooling, the solution was diluted with sulfuric acid (1N;70 ml), washed with ether, neutralized (4N; sodium hydroxide solution followed by pH 6.5 buffer) and extracted into dichloromethane (3×50 ml). Combined extracts were dried (MgSO$_4$) and evaporated to give a solid. Purification by chromatography [Fluka HF$_{254}$ SiO$_2$] eluting with dichloromethane:ethanol:ammonia (100:100:1) gave the title compound (190 mg) as a white foam. T.l.c. SiO$_2$ [dichloromethane: ethanol (1:1), 1% NH$_3$] Rf 0.55. [α]$_D^{20}$ = +27.88° (chloroform). I.r. (Nujol) 3300, 1720, 1575 cm$^{-1}$.

EXAMPLE 9

[1S-[1α(Z),2β,5β]]-6-[[2-(Hexahydro-1H-azepin-1-yl)-5-[κ2'-(hydroxymethyl)[1,1'-biphenyl]-4-yl]methoxy]cyclopentyl]oxy]-4-hexenoic acid Using Intermediate 40 (250 mg) and 1,3-dihydro-1-hydroxy-2,1-benzoxaborole (170 mg) and identical conditions to those employed in Example 8 above except that additional chromatography was required using triethylamine in place of ammonia gave the title compound (150 mg) as a white foam. T.l.c. SiO$_2$ [dichloromethane:ethanol (1:1), 1% NH$_3$] Rf 0.55. [α]$_D^{20}$ = −29.77° (chloroform). I.r. (Nujol) 3300, 1720, 1575 cm$^{-1}$.

The term "active ingredient" as used below refers to a compound of the invention and may be, for example, a compound according to one of the previous examples, such as [1α(Z),2β,5β]-6-[[2-(hexahydro-1H-azepin-1-yl)-5-[[2'-(hydroxymethyl)[1,1'-biphenyl]-4-yl]methoxy]cyclopentyl]oxy]-4-hexenoic acid or a physiologically acceptable salt, solvate or cyclodextrin (e.g. β-cyclodextrin) complex thereof.

PHARMACEUTICAL EXAMPLES (i) Tablets

These may be prepared by direct compression or wet granulation. The direct compression method is preferred but may not be suitable in all cases as it is dependent upon the dose level and physical characteristics of the active ingredient.

| A. Direct Compression | mg/tablet |
|---|---|
| Active Ingredient | 100.00 |
| Microcrystalline Cellulose NF | 298.00 |
| Magnesium Stearate BP | 2.00 |
| Compression Weight | 400.00 mg |

The active ingredient is sieved through a 250 μm sieve, blended with the excipients and compressed using 10.0 mm punches. Tablets of other strengths may be prepared by altering the compression weight and using punches to suit.

| B. Wet Granulation | mg/tablet |
|---|---|
| Active Ingredient | 100.00 |
| Lactose BP | 238.00 |
| Starch BP | 40.00 |
| Pregelatinized Maize Starch BP | 20.00 |
| Magnesium Stearate BP | 2.00 |
| Compressed Weight | 400.00 mg |

The active ingredient is sieved through a 250 μm sieve and blended with the lactose, starch and pregelatinised starch. The mixed powders are moistened with purified water, granules are made, dried, screened and blended with the magnesium stearate. The lubricated granules are compressed into tablets as described for the direct compression formula.

The tablets may be film coated with suitable film forming materials, e.g. methyl cellulose or hydroxypropyl methyl cellulose using standard techniques. Alternatively the tablets may be sugar coated.

(ii) Capsules

|  | mg/capsule |
|---|---|
| Active Ingredient | 100.00 |
| *STA-RX 1500 | 99.00 |
| Magnesium Stearate BP | 1.00 |
| Fill Weight | 200.00 mg |

*A form of directly compressible starch supplied by Colorcorn Ltd., Orpington, Kent.

The active ingredient is sieved through a 250 μm sieve and blended with the other materials. The mix is filled into No. 2 hard gelatin capsules using a suitable filling machine. Other doses may be prepared by altering the fill weight and if necessary, changing the capsule size to suit.

(iii) Inhalation cartridges

|  | mg/cartridge |
|---|---|
| Active Ingredient (micronized) | 3.00 |
| Lactose BP to | 25.00 |

The active ingredient is micronized in a fluid energy mill to a fine particle size range prior to blending with normal tabletting grade lactose in a high energy mixer. The powder blend is filled into No. 3 hard gelatin capsules on a suitable encapsulating machine.

The contents of the cartridge are administered using a powder inhaler.

(iv) Metered Dose Pressurized Aerosol

|  | mg/metered dose | Per Can |
|---|---|---|
| Active Ingredient (micronized) | 0.500 | 120 mg |
| Oleic Acid BP | 0.050 | 12 mg |
| Trichlorofluoromethane BP | 22.25 | 5.34 g |
| Dichlorodifluoromethane BP | 60.90 | 14.62 g |

The active ingredient is micronized in a fluid energy mill to a fine particle size range. The oleic acid is mixed with the trichlorofluoromethane at a temperature of 10°–15° and the micronized drug is mixed into this solution with a high shear mixer. The suspension is metered into aluminum aerosol cans and suitable metering valves, delivering a metered dose of 85 mg of suspension, are crimped onto the cans and the dichlorodifluoromethane is pressure filled into the cans through the valves.

(v) Syrup

|  | mg/5 ml dose |
|---|---|
| Active Ingredient | 100.00 |
| Buffer |  |
| Flavour |  |
| Colour | as required |
| Preservative |  |
| Thickening Agent |  |
| Sweetening Agent |  |
| Purified Water to | 5.00 ml |

The active ingredient, buffer, flavor, color, preservative, thickening agent and sweetening agent are dissolved in some of the water, the solution is adjusted to volume and mixed. The syrup produced is clarified by filtration.

(vi) Injection for Intravenous Administration

| Active Ingredient | 50 mg |
|---|---|
| Water for injections BP to | 5 ml |

Sodium chloride or any other suitable material may be added to adjust the tonicity of the solution and the pH may be adjusted to that of maximum stability of the active ingredient using dilute acid or alkali or by the addition of suitable buffer salts. The solution is prepared, clarified and filled into appropriate sized ampoules sealed by fusion of the glass. The injection is sterilized by heating in an autoclave using one of the acceptable cycles. Alternatively the solution may be sterilized by filtration and filled into sterile ampoules under aseptic conditions. The solution may be packed under an inert atmosphere of nitrogen.

(vi) Suspensions

|  | mg/5 ml dose |
|---|---|
| Active Ingredient | 100.00 |
| Aluminium monostearate | 75.00 |
| Sweetening agent |  |
| Flavour | as required |

| -continued | |
|---|---|
| | mg/5 ml dose |
| Colour | |
| Fractionated coconut oil to | 5.00 ml |

The aluminum monostearate is dispensed in about 90% of the fractionated coconut oil. The resulting suspension is heated to 115° while stirring and then cooled. The sweetening agent, flavor and color are added and the active ingredient is suitably dispersed. The suspension is made up to volume with the remaining fractionated coconut oil and mixed.

We claim:

1. Compounds of the general formula (1)

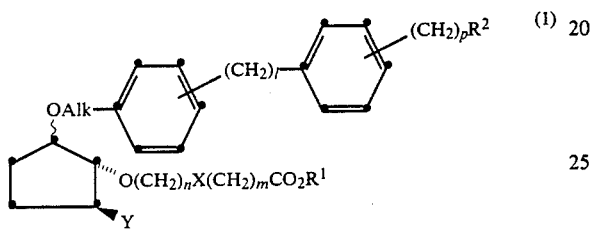

wherein:

$R^2$ is a hydrogen atom or a methyl group;

X is cis or trans —CH=CH— or —CH$_2$CH$_2$—, m is 2, 3 or 4 and n is 1; or X is trans —CH=CH—, m is zero and n is 3;

Y is pyrrolidino, piperidino, morpholino, piperazino, thiomorpholino, 1,1-dioxothiomorpholino, homomorpholino or hexamethyleneimino optionally substituted by one or more $C_{1-4}$ alkyl groups; and wherein said Y group is attached to the cyclopentane ring via a nitrogen atom;

Alk is a straight or branched $C_{1-5}$ alkyl chain;

l is zero or 1;

p is zero, 1, 2, 3 or 4;

$R^2$ is a hydroxyl group or a group selected from —OCOR$^3$, —CO$_2$R$^3$, —CONR$^3$R$^4$, —SO$_2$NR$^3$R$^4$, —NHCOR$^3$, —NHSO$_2$R$^5$, —SO$_2$R$^5$, —SR$^5$, —NR$^3$R$^4$, —COR$^5$, —NHCONR$^3$R$^4$ and —NHCSNH$_2$;

$R^3$ and $R^4$, which may be the same or different, represent a hydrogen atom or a $C_{1-4}$alkyl or $C_{1-10}$aralkyl group; and $R^5$ is a $C_{1-4}$alkyl group; and the physiologically acceptable salts, solvates and cyclodextrin complexes thereof.

2. Compounds as claimed in claim 1 in which Y is pyrrolidino, piperidino, morpholino, homomorpholino or hexamethyleneimino.

3. Compounds as claimed in claim 1 in which n is 1, m is 2 and $R^1$ is a hydrogen atom.

4. Compounds as claimed in claim 1 in which the group

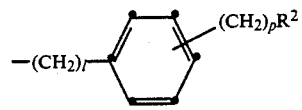

is attached at the para position of the phenyl group in the rest of the molecule, l represents zero and p is zero, 1 or 2.

5. Compounds as claimed in claim 1, having the formula (1C)

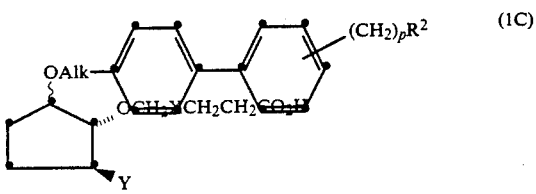

and the physiologically acceptable salts, solvates and cyclodextrin complexes thereof, wherein X is cis or trans —CH=CH— or —CH$_2$CH$_2$—, Y is pyrrolidino, piperidino, morpholino, homomorpholino or hexamethyleneimino, Alk is a straight $C_{1-3}$alkyl chain, p is zero, 1 or 2 and $R^2$ is —OH, —CO$_2$H, —CONH$_2$, —NHCOCH$_3$, —NHSO$_2$CH$_3$, —SO$_2$NHCH$_3$, —NHCONH$_2$ or —SO$_2$CH$_3$.

6. Compounds of formula (1A) as claimed in claim 1 in which the carbon atom carrying the α-side chain is in the R configuration.

7. Compounds as claimed in claim 1, said compounds being: p0 [1α(Z),2β,5β]-(±)-6-[[2-(hexahydro-1H-azepin-1yl)-5-[[2'-(hydroxymethyl) [1,1'-biphenyl]-4-yl]methoxy]cyclopentyl]oxy]-4-hexenoic acid, or a physiologically acceptable salt, solvate or cyclodextrin complex thereof.

8. Compounds as claimed in claim 1, said compounds being:

[1R-[1α(Z),2β,5β]]-6-[[2-(hexahydro-1H-azepin-1-yl)-5-[[2'-(hydroxymethyl) [1,1'-biphenyl]-4-yl]methoxy]cyclopentyl]oxy]-4-hexenoic acid, or a physiologically acceptable salt, solvate or cyclodextrin complex thereof.

9. Compounds as claimed in claim 1, said compounds being:

[1S-[1α(Z),2β,5β]]-6-[[2-(hexahydro-1H-azepin-1 yl)-5-[[2'-(hydroxymethyl) [1,1'-biphenyl]-4-yl]methoxy]cyclopentyl]oxy]-4-hexenoic acid, or a physiologically acceptable salt, solvate or cyclodextrin complex thereof.

10. A pharmaceutical composition comprising an effective amount of a compound as claimed in claim 1 together with one or more pharmaceutical carriers.

11. A method for the treatment or prevention of occlusive vascular diseases which comprises administering to the patient an effective amount of a compound as claimed in claim 1 or a physiologically acceptable salt, solvate or cyclodextrin complex thereof.

* * * * *